United States Patent
Wang et al.

(10) Patent No.: US 7,276,487 B2
(45) Date of Patent: Oct. 2, 2007

(54) 9A, 11-3C-BICYCLIC 9A-AZALIDE DERIVATIVES

(75) Inventors: Guoqiang Wang, Belmont, MA (US); Yulin Peng, Waltham, MA (US); Yanchun Wang, Newton, MA (US); Ly Tam Phan, Quincy, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 232 days.

(21) Appl. No.: 10/946,339

(22) Filed: Sep. 21, 2004

(65) Prior Publication Data

US 2005/0090460 A1    Apr. 28, 2005

Related U.S. Application Data

(60) Provisional application No. 60/560,735, filed on Sep. 23, 2003.

(51) Int. Cl.
*A61K 31/70*    (2006.01)
*C07H 17/08*    (2006.01)

(52) U.S. Cl. .......................................... 514/29; 536/7.4
(58) Field of Classification Search ................ 536/7.4, 536/18.5; 514/29
See application file for complete search history.

(56) References Cited

U.S. PATENT DOCUMENTS

| | | | |
|---|---|---|---|
| 4,474,768 A | 10/1984 | Bright | |
| 4,492,688 A * | 1/1985 | Bright | ........................... 514/29 |
| 4,517,359 A | 5/1985 | Kobrehel et al. | |
| 4,990,602 A | 2/1991 | Morimoto et al. | |
| 5,403,923 A | 4/1995 | Kashimura et al. | |
| 5,444,051 A | 8/1995 | Agouridas et al. | |
| 5,527,780 A | 6/1996 | Agouridas et al. | |
| 5,631,355 A | 5/1997 | Asaka et al. | |
| 5,686,587 A | 11/1997 | Yang | |
| 5,866,549 A | 2/1999 | Or et al. | |
| 5,969,161 A | 10/1999 | Bonnet et al. | |
| 6,046,171 A | 4/2000 | Or et al. | |
| 6,110,965 A | 8/2000 | Lazarevski et al. | |
| 6,124,269 A | 9/2000 | Phan et al. | |
| 6,399,582 B1 | 6/2002 | Hlasta et al. | |
| 6,518,251 B1 * | 2/2003 | Cheng et al. | ................ 514/29 |
| 6,645,941 B1 | 11/2003 | Wang et al. | |
| 6,764,998 B1 * | 7/2004 | Wang et al. | ................... 514/29 |

FOREIGN PATENT DOCUMENTS

| | | |
|---|---|---|
| EP | 0 283 055 A2 | 9/1988 |
| WO | WO93/13116 | 7/1993 |
| WO | WO98/56801 | 12/1998 |
| WO | WO98/56802 | 12/1998 |
| WO | WO99/00124 | 1/1999 |
| WO | WO99/00125 | 1/1999 |
| WO | WO99/20639 | 4/1999 |
| WO | WO 01/14397 A1 | 3/2001 |
| WO | WO 02/12260 A1 | 2/2002 |
| WO | WO 02/055531 A1 | 7/2002 |
| WO | WO 03/042228 A1 | 5/2003 |

OTHER PUBLICATIONS

Bright, G. Michael, et al., "Synthesis, *In Vitro* and *In Vivo* Activity of Novel 9-Deoxo-9a-Aza-9a-Homoerythromycin A Derivatives; A New Class of Macrolide Antibiotics, the Azalides," *J. of Antibiotics*, vol. XLI(8): 1029-1047 (1988).

* cited by examiner

*Primary Examiner*—Elli Peselev
(74) *Attorney, Agent, or Firm*—Suanne Nakajima; Carolyn S. Elmore; Elmore Patent Law Group

(57) ABSTRACT

The present invention discloses compounds of formula I, or pharmaceutically acceptable salts, esters, or prodrugs thereof:

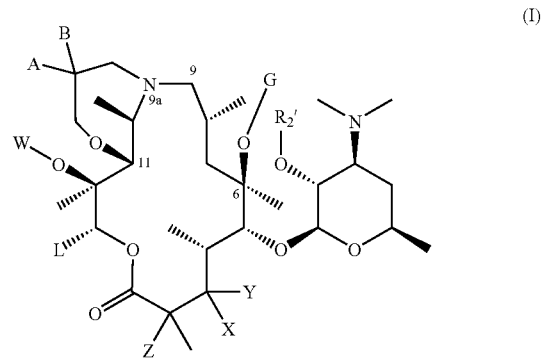

which exhibit antibacterial properties. The present invention further relates to pharmaceutical compositions comprising the aforementioned compounds for administration to a subject in need of antibiotic treatment. The invention also relates to methods of treating a bacterial infection in a subject by administering a pharmaceutical composition comprising the compounds of the present invention. The invention further includes process by which to make the compounds of the present invention.

18 Claims, No Drawings

9A, 11-3C-BICYCLIC 9A-AZALIDE DERIVATIVES

RELATED APPLICATION

This application claims the benefit of U.S. Provisional Application No. 60/560,735, filed on Sep. 23, 2003. The entire teachings of the above application are incorporated herein by reference.

TECHNICAL FIELD

The present invention relates to novel semisynthetic macrolides having antibacterial activity and useful in the treatment and prevention of bacterial infections. More particularly, the invention relates to 9a,11-3C-bicyclic 9a-azalide derivatives, compositions comprising such compounds, methods for using the same, and processes by which to make such compounds.

BACKGROUND OF THE INVENTION

Macrolide antibacterial agents are widely used to treat and prevent bacterial infections. However, the discovery of bacterial strains which have resistance or insufficient susceptibility to macrolide antibacterial agents has promoted the development of compounds with modified or improved profiles of antibiotic activity. One such class of compounds is azalides, which includes azithromycin, described in U.S. Pat. Nos. 4,474,768 and 4,517,359. Azalides are macrolide antibacterial agents with a ring structure similar to the erythronolide A or B, however azalides possess a substituted or unsubstituted nitrogen moiety at the 9a position as illustrated in the following structure:

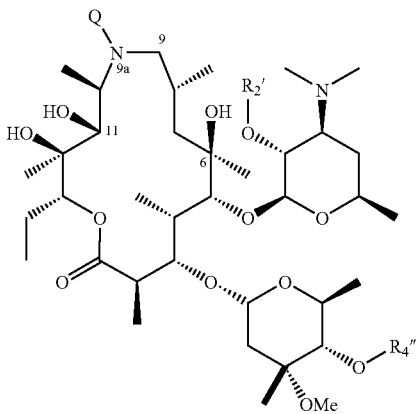

The potential for azalides to display modified or improved profiles for antibiotic activity has spawned extensive research to identify additional azalide derivatives with enhanced clinical properties. The following are examples of current efforts in azalide research:

PCT Application WO98/56801, published Dec. 17, 1998 discloses a series of 9a-(N-(alkyl))-azalide erythromycin A derivatives and a series of 9a-(N-(alkyl))-azalide 6-O-methylerythromycin A derivatives;

PCT Application WO98/56802, published Dec. 17, 1998 discloses a series of 9a-(N—(H))-azalide erythromycin A derivatives and a series of 9a-(N—(H))-azalide 6-O-methylerythromycin A derivatives;

PCT Application WO99/00124, published Jan. 7, 1999 discloses a series of 9a-(N—($R_n$))-azalide 3-thioxoerythromycin A derivatives and a series of 9a-(N—($R_n$))-azalide 6-O-methyl 3-oxoerythromycin A derivatives, wherein $R_n$ is an optionally substituted alkyl or heteroalkyl;

PCT Application WO99/00125, published Jan. 7, 1999 discloses a series of 9a-(N—($R_n$))-azalide 3-oxoerythromycin A derivatives and a series of 9a-(N—($R_n$))-azalide 6-O-methyl 3-oxoerythromycin A derivatives, wherein $R_n$ is an optionally substituted alkyl or heteroalkyl; and U.S. Pat. No. 5,686,587 discloses a synthesis of azithromycin comprising introducing a 9a-(N(H))-moiety to erythromycin A by oxime formation, Beckmann rearrangement, reduction, and methylation.

Additional disclosures delineating 15-membered azalide derivatives include, but are not limited to: PCT Application No. WO01/14397 (2001); PCT Application No. WO03/042228 (2003); PCT Application No. WO02/12260 (2002); U.S. Pat. No. 6,110,965 (2000); European Application No. 0 283 055 (1990); PCT Application No. WO99/20639 (1999); PCT Application No. WO02/055531 (2002); and PCT Application No. WO93/13116 (1993).

SUMMARY OF THE INVENTION

The present invention provides a novel class of 9a,11-3C-bicyclic 9a-azalide compounds, or pharmaceutically-acceptable salts, esters, or prodrugs thereof. The present invention further relates to pharmaceutical compositions, comprising the compounds of the present invention, for administration to a subject in need of antibiotic treatment. The invention also relates to methods of treating a bacterial infection in a subject by administering compounds or of a pharmaceutical composition comprising the compounds of the present invention. The invention further includes process by which to make the compounds of the present invention.

In one embodiment of the present invention there are disclosed compounds of formula I:

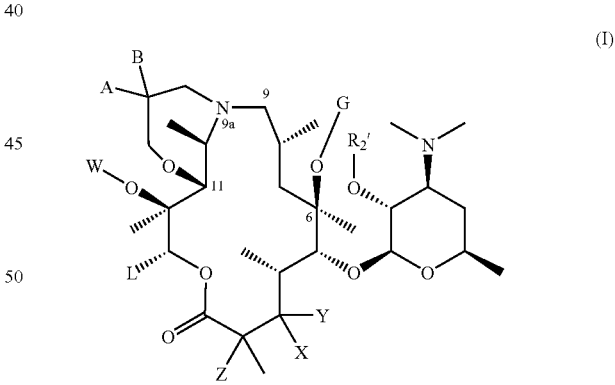

(I)

as well as the pharmaceutically acceptable salts, esters and prodrugs thereof, wherein:

A is
  (a) —$OR_p$, where $R_p$ is a hydroxy protecting group;
  (b) —$R_1$, where $R_1$ is independently aryl, substituted aryl, heteroaryl, or substituted heteroaryl;
  (c) —$OR_1$, where $R_1$ is as previously defined;
  (d) —$R_2$, where $R_2$ independently is
    (1) hydrogen;
    (2) —$C_1$-$C_6$ alkyl containing 0, 1, 2, or 3 heteroatoms selected from O, S or N, optionally substituted with one or more substituents selected from halogen, aryl, substituted aryl, heteroaryl, or substituted heteroaryl;
(3) —$C_2$-$C_6$ alkenyl containing 0, 1, 2, or 3 heteroatoms selected from O, S, or N, optionally substituted with one or more substituents selected from halogen, substituted aryl, heteroaryl, or substituted heteroaryl; or
(4) —$C_2$-$C_6$ alkynyl containing 0, 1, 2, or 3 heteroatoms selected from O, S or N, optionally substituted with one or more substituents selected from halogen, aryl, substituted aryl, heteroaryl, or substituted heteroaryl;
(e) —$OR_2$, where $R_2$ is previously defined;
(f) —$S(O)_nR_{11}$, where n=0, 1 or 2, and $R_{11}$ is independently $R_1$ or $R_2$, where $R_1$ and $R_2$ are as previously defined;
(g) —$NHC(O)R_{11}$, where $R_{11}$ is as previously defined;
(h) —$NHC(O)NHR_{11}$, where $R_{11}$ is as previously defined;
(i) —$NHS(O)_2R_{11}$, where $R_{11}$ is as previously defined;
(j) —$NR_{14}R_{15}$, where $R_{14}$ and $R_{15}$ are each independently $R_{11}$, where $R_{11}$ is as previously defined; or
(k) —$NHR_3$, where $R_3$ is an amino protecting group;

B is
(a) deuterium;
(b) halogen;
(c) —OH;
(d) —$R_1$, where $R_1$ is as previously defined;
(e) —$R_2$, where $R_2$ is as previously defined; or
(f) —$OR_p$, where $R_p$ is as previously defined, provided that when B is halogen, —OH or $OR_p$, A is $R_1$ or $R_2$, where $R_1$ and $R_2$ are previously defined;

or, alternatively, A and B taken together with the carbon atom to which they are attached are
(a) C=O;
(b) $C(OR_2)_2$, where $R_2$ is as previously defined;
(c) $C(SR_2)_2$, where $R_2$ is as previously defined;
(d) $C(OR_{12})(OR_{13})$, where $R_{12}$ and $R_{13}$ taken together are —$(CH_2)_m$—, and where m is 2 or 3;
(e) $C(SR_{12})(SR_{13})$, where $R_{12}$ and $R_{13}$ taken together are —$(CH_2)_m$—, where m is as previously defined;
(f) C=$CHR_{11}$, where $R_{11}$ is as previously defined;
(g) C=N—O—$R_{11}$, where $R_{11}$ is as previously defined;
(h) C=$NNHR_{11}$, where $R_{11}$ is as previously defined;
(i) C=$NNHC(O)R_{11}$, where $R_{11}$ is as previously defined;
(j) C=$NNHC(O)NHR_{11}$, where $R_{11}$ is as previously defined;
(k) C=$NNHS(O)_2R_{11}$, where $R_{11}$ is as previously defined;
(l) C=$NNHR_3$, where $R_3$ is as previously defined; or
(m) C=$NR_{11}$, where $R_{11}$ is as previously defined;

G is
(a) hydrogen;
(b) —$C_1$-$C_6$ alkyl, containing 0, 1, 2, or 3 heteroatoms selected from O, S or N, optionally substituted with one or more substituents selected from halogen, aryl, substituted aryl, heteroaryl, or substituted heteroaryl;
(c) —$C_2$-$C_6$ alkenyl, containing 0, 1, 2, or 3 heteroatoms selected from O, S or N, optionally substituted with one or more substituents selected from halogen, aryl, substituted aryl, heteroaryl, or substituted heteroaryl;
(d) —$C_2$-$C_6$ alkynyl, containing 0, 1, 2, or 3 heteroatoms selected from O, S or N, optionally substituted with one or more substituents selected from halogen, aryl, substituted aryl, heteroaryl, or substituted heteroaryl;

L is
(a) —$CH(OH)CH_3$;
(b) —$C_1$-$C_6$ alkyl, optionally substituted with one or more substituents selected from aryl, substituted aryl, heteroaryl, or substituted heteroaryl;
(c) —$C_2$-$C_6$ alkenyl, optionally substituted with one or more substituents selected from aryl, substituted aryl, heteroaryl, or substituted heteroaryl; or
(d) —$C_2$-$C_6$ alkynyl, optionally substituted with one or more substituents selected from aryl, substituted aryl, heteroaryl, or substituted heteroaryl;

W is selected from:
(a) hydrogen;
(b) $R_8$, where $R_8$ is $C_1$-$C_6$-alkyl, $C_2$-$C_6$-alkenyl or $C_2$-$C_6$-alkynyl, optionally substituted with one or more substituents selected from:
(1) halogen;
(2) aryl;
(3) substituted-aryl;
(4) heteroaryl;
(5) substituted-heteroaryl;
(6) —O—$C_1$-$C_6$-alkyl-$R_{11}$, where $R_{11}$ is as previously defined; and
(7) —$N(R_{14}R_{15})$, where $R_{14}$ and $R_{15}$ are as previously defined;
(c) —$C(O)R_{11}$, where $R_{11}$, where $R_{11}$ is as previously defined;
(d) —$C(O)O$—$R_{11}$, where $R_{11}$ is as previously defined; and
(e) —$C(O)N(R_{14}R_{15})$, where $R_{14}$ and $R_{15}$ are as previously defined;

X is hydrogen;
Y is
(a) hydrogen;
(b) —OH;
(c) —$OR_p$, where $R_p$ is as previously defined;
(d) —$OR_{11}$, where $R_{11}$, is as previously defined;
(e) —$OC(O)R_{11}$, where $R_{11}$ is as previously defined;
(f) —$OC(O)NHR_{11}$, where $R_{11}$ is as previously defined;
(g) —$S(O)_nR_{11}$, where n and $R_{11}$ are as previously defined;

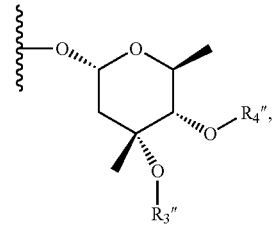

(h)

where $R_3''$ is selected from hydrogen or methyl and $R_4''$ is selected from:
(1) hydrogen;
(2) $R_p$, where $R_p$ is as previously defined; or
(3) —$C(O)(CH_2)_k$-M-$R_{11}$, wherein $R_{11}$ is as previously defined, k is 2 to 8, and M is absent or -$Q(CH_2)_qQ'$-, where q=an integer from 2 to 8, and Q and Q' are independently selected from:
i) —$N(R_{20})$—, where $R_{20}$ is $R_{11}$ is as previously defined;
ii) —O—;
iii) —$S(O)_n$—, where n is as previously defined;
iv) —$N(R_{20})C(O)$—, where $R_{20}$ is as previously defined;

v) —C(O)N($R_{20}$)—, where $R_{20}$ is as previously defined; or vi) —N[C(O)$R_{20}$]—, where $R_{20}$ is as previously defined; and in the alternative, X and Y combined together are oxo;

Z is
  (a) hydrogen;
  (b) methyl; or
  (c) halogen; and $R_2$' is hydrogen or $R_p$, where $R_p$, is as previously defined.

In another embodiment of the present invention there are disclosed pharmaceutical compositions comprising a therapeutically effective amount of a compound of the invention in combination with a pharmaceutically acceptable carrier or excipient. In yet another embodiment of the invention are methods of treating antibacterial infections in a subject in need of such treatment with said pharmaceutical compositions. Suitable carriers and formulations of the compounds of the present invention are disclosed.

DETAILED DESCRIPTION OF THE INVENTION

A first embodiment of the present invention is a compound of formula I as illustrated above, or a pharmaceutically acceptable salt, ester or prodrug thereof.

Preferred subgenera of the present invention are:

A compound of formula II:

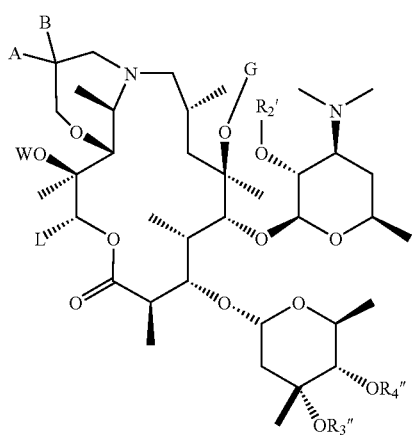

(II)

wherein A, B, G, L, W, $R_2$', $R_3$", and $R_4$" are as previously defined;

A compound of formula III:

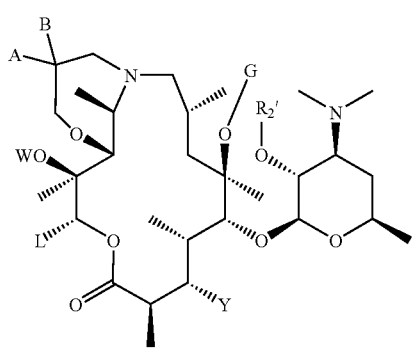

(III)

wherein A, B, G, L, W, Y, and $R_2$' are as previously defined;

A compound of formula IV:

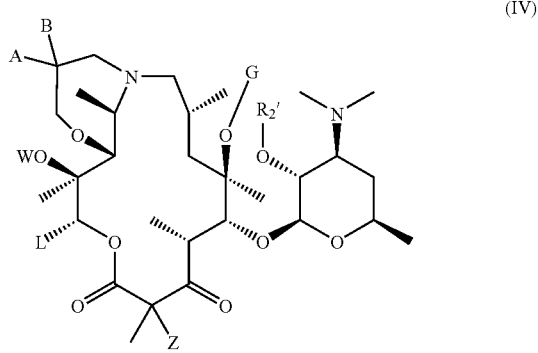

(IV)

wherein A, B, G, L, W, Z, and $R_2$' are as previously defined;

A compound of formula V:

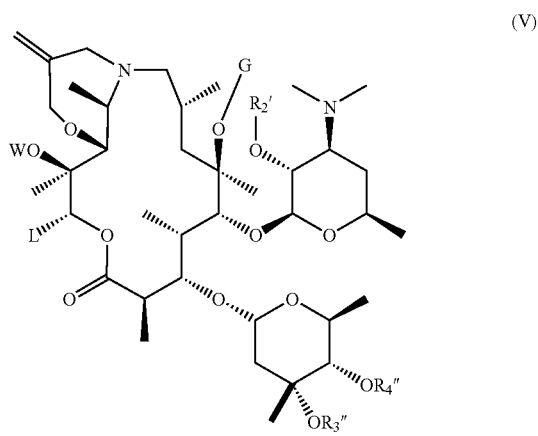

(V)

wherein G, L, W, $R_2$', $R_3$", and $R_4$" are as previously defined;

A compound of formula VI:

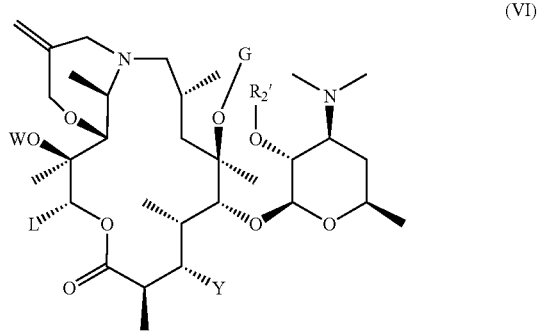

(VI)

wherein G, L, W, Y, and $R_2$' are as previously defined; and

A compound of formula VII:

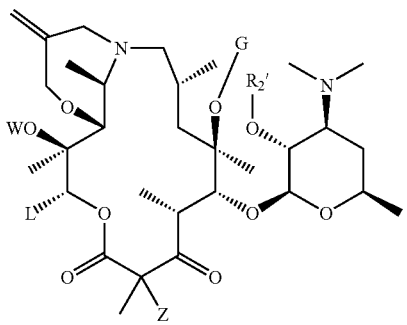

(VII)

wherein G, L, W, Z, and $R_2'$ are as previously defined.

Representative compounds according to the invention are those selected from:

(a) Compound of formula II, wherein A and B taken together with the carbon atom to which they are attached are C=$CH_2$, L is —$CH_2CH_3$, G=W=$R_2'$=$R_4''$=hydrogen, and $R_3''$ is methyl;

(b) Compound of formula II, wherein A and B taken together with the carbon atom to which they are attached are C=$CH_2$, L is —$CH_2CH_3$, G=W=$R_4''$=hydrogen, $R_2'$ is Ac, and $R_3''$ is —$CH_3$;

(c) Compound of formula II, wherein A is hydrogen, B is —$CH_3$, L is —$CH_2CH_3$, G=W=$R_2'$=$R_4''$=hydrogen, and $R_3''$ is —$CH_3$;

(d) Compound of formula V, wherein L is —$CH_2CH_3$, G=W=$R_4''$=hydrogen, $R_2'$=$R_4''$=Ac, and $R_3''$ is —$CH_3$;

(e) Compound of formula VI, wherein L is —$CH_2CH_3$ Y is hydroxy, and G=W=$R_2'$=hydrogen;

(f) Compound of formula VI, wherein L is —$CH_2CH_3$, Y is hydroxy, G=W=hydrogen, and $R_2'$=TES;

(g) Compound of formula VI, wherein L is —$CH_2CH_3$, Y is hydroxy, G=W=hydrogen, and $R_2'$=Ac;

(h) Compound of formula VI, L is —$CH_2CH_3$, G=W=hydrogen, $R_2'$ is Ac, and Y is (quinolin-3-yl)-allyloxy;

(i) Compound of formula VI, L is —$CH_2CH_3$, G=W=$R_2'$=hydrogen, and Y is (quinolin-3-yl)-allyloxy;

(j) Compound of formula V, wherein L is —$CH_2CH_3$, W is —$CH_2CH$=$CH_2$, G is hydrogen, $R_2'$=$R_4''$=Ac, and $R_3''$ is —$CH_3$;

(k) Compound of formula VI, wherein L is —$CH_2CH_3$, W is —$CH_2CH$=$CH_2$, G=hydrogen, Y is hydroxy, and $R_2'$ is Ac;

(l) Compound of formula VI, wherein L is —$CH_2CH_3$, W is —$CH_2CH$=$CH_2$, Y is hydroxy, and G=$R_2'$=hydrogen;

(m) Compound of formula I, wherein A and B are taken together with the carbon atom to which they are attached to form C=$CH_2$, L is —$CH_2CH_3$, W=G=Z=$R_2'$=hydrogen, and X and Y taken together are oxo;

(n) Compound of formula I, wherein A and B are taken together with the carbon atom to which they are attached to form C=$CH_2$, L is —$CH_2CH_3$, W=X=G=Z=hydrogen, $R_2'$=Ac, and Y is —OC(O)(p-nitrophenyl);

(o) Compound of formula I, wherein A and B are taken together with the carbon atom to which they are attached to form C=$CH_2$, L is —$CH_2CH_3$, W=X=G=Z=$R_2'$=hydrogen, and Y is —OC(O)(p-nitrophenyl);

(p) Compound of formula I, wherein A and B are taken together with the carbon atom to which they are attached to form C=$CH_2$, L is —$CH_2CH_3$, W=X=G=Z=hydrogen, $R_2'$=Ac, and Y is —OC(O)(2-nitro-4-trifluoromethylphenyl);

(q) Compound of formula I, wherein A and B are taken together with the carbon atom to which they are attached to form C=$CH_2$, L is —$CH_2CH_3$, W=X=G=Z=$R_2'$=hydrogen, and Y is —OC(O)(2-nitro-4-trifluoromethylphenyl);

(r) Compound of formula I, wherein A and B are taken together with the carbon atom to which they are attached to form C=$CH_2$, L is —$CH_2CH_3$, W=X=G=Z=hydrogen, $R_2'$=Ac, and Y is —OC(O)$CH_2$(p-methoxyphenyl); and (s) Compound of formula I, wherein A and B are taken together with the carbon atom to which they are attached to form C=$CH_2$, L is —$CH_2CH_3$, W=X=G=Z=$R_2'$=hydrogen, and Y is —OC(O)$CH_2$(p-methoxyphenyl).

A further embodiment of the present invention includes pharmaceutical compositions comprising any single compound delineated herein, or a pharmaceutically acceptable salt, ester, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, or prodrug thereof, with a pharmaceutically acceptable carrier or excipient.

Yet a further embodiment of the present invention is a pharmaceutical composition comprising any single compound delineated herein in combination with one or more antibiotics known in the art (such as penicillin, amoxicillin, azithromycin, erythromycin, ciproflaxin, telithromycin, cethromycin, and the like) or a pharmaceutically acceptable salt, ester, or prodrug thereof, with a pharmaceutically acceptable carrier or excipient.

An additional embodiment of the present invention is a method of treating bacterial infections in a subject in need of such treatment through administration to said subject a compound or composition of the present invention.

Yet another embodiment of the present invention is a method of treating bacterial infections in a subject in need of such treatment through the concurrent administration of a compound or composition of the present invention and another antibiotic known in the art.

In addition, the present invention contemplates processes of making any compound delineated herein via any synthetic method delineated herein.

Definitions

Listed below are definitions of various terms used to describe this invention. These definitions apply to the terms as they are used throughout this specification and claims, unless otherwise limited in specific instances, either individually or as part of a larger group.

The terms "$C_1$-$C_3$ alkyl," "$C_1$-$C_6$ alkyl," or "$C_1$-$C_{12}$ alkyl," as used herein, refer to saturated, straight- or branched-chain hydrocarbon radicals containing between one and three, one and six, or one and twelve carbon atoms, respectively. Examples of $C_1$-$C_3$ alkyl radicals include methyl, ethyl, propyl and isopropyl radicals; examples of $C_1$-$C_6$ alkyl radicals include, but are not limited to, methyl, ethyl, propyl, isopropyl, n-butyl, tert-butyl, neopentyl and n-hexyl radicals; and examples of $C_1$-$C_{12}$ alkyl radicals include, but are not limited to, ethyl, propyl, isopropyl, n-hexyl, octyl, decyl, dodecyl radicals.

The term "substituted alkyl," as used herein, refers to a "$C_2$-$C_{12}$ alkyl" or "$C_1$-$C_6$ alkyl" group as previously defined, substituted by independent replacement of one, two, or three of the hydrogen atoms thereon with substituents including, but not limited to, —F, —Cl, —Br, —I, —OH, protected hydroxy, —$NO_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$-$C_{12}$-alkyl, —NHC(NH)NH—$C_2$-$C_{12}$-alkenyl, —NHC(O)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(H)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)-$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$—aryl, —$SO_2NH$-heteroaryl, —$SO_2NH$—heterocycloalkyl, —$NHSO_2$—$C_1$-$C_{12}$-alkyl, —$NHSO_2$—$C_2$-$C_{12}$-alkenyl, $NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocyloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The terms "$C_2$-$C_{12}$ alkenyl" or "$C_2$-$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "substituted alkenyl," as used herein, refers to a "$C_2$-$C_{12}$ alkenyl" or "$C_2$-$C_6$ alkenyl" group as previously defined, substituted by independent replacement of one, two, or three of the hydrogen atoms thereon with substituents including, but not limited to, —F, —Cl, —Br, —I, —OH, protected hydroxy, —$NO_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(H)—$C_1$-$C_{12}$, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_2$-alkenyl, —S—C$_3$-C$_{12}$-cycloalkyl, —S-aryl, —S-heteroaryl, —S-heterocycloalkyl, or methylthiomethyl.

The terms "C$_2$-C$_{12}$ alkynyl" or "C$_2$-C$_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "C$_2$-C$_{12}$ alkynyl" or "C$_2$-C$_6$ alkynyl" group as previously defined, substituted by independent replacement of one, two, or three of the hydrogen atoms thereon with substituents including, but not limited to, —F, —Cl, —Br, —I, —OH, protected hydroxy, —NO$_2$, —CN, —C$_1$-C$_{12}$-alkyl optionally substituted with halogen, C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_2$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(H)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH— aryl, —SO$_2$NH— heteroaryl, —SO$_2$NH— heterocycloalkyl, —NHSO$_2$—C$_1$-C$_{12}$-alkyl, —NHSO$_2$—C$_2$-C$_{12}$-alkenyl, NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

The term "C$_1$-C$_6$ alkoxy," as used herein, refers to a C$_1$-C$_6$ alkyl group, as previously defined, attached to the parent molecular moiety through an oxygen atom. Examples of C$_1$-C$_6$-alkoxy include, but are not limited to, methoxy, ethoxy, propoxy, isopropoxy, n-butoxy, tert-butoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by independent replacement of one, two, or three of the hydrogen atoms thereon with substituents including, but not limited to, —F, —Cl, —Br, —I, —OH, protected hydroxy, —NO$_2$, —CN, —C$_1$-C$_{12}$-alkyl optionally substituted with halogen, C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—$C_2$-$C_2$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_2$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_2$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$-$C_{12}$-alkyl, —NHC(NH)NH—$C_2$-$C_{12}$-alkenyl, —NHC(NH)NH—$C_2$-$C_2$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$, —NHC(NH)—$C_2$-$C_{12}$-alkenyl, —NHC(NH)—$C_2$-$C_2$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_2$-alkenyl, —C(NH)NH—$C_3$-$C_2$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_2$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "arylalkyl," as used herein, refers to a $C_1$-$C_3$ alkyl or $C_1$-$C_6$ alkyl substituted with an aryl ring. Examples include, but are not limited to, benzyl, phenethyl and the like.

The term "substituted arylalkyl," as used herein, refers to an arylalkyl group, as previously defined, substituted by independent replacement of one, two, or three of the hydrogen atoms thereon with substituents including, but not limited to, but not limited to, —F, —Cl, —Br, —I, —OH, protected hydroxy, —NO$_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, NHC(O)NH—$C_1$-$C_{12}$-alkyl, —NHC(O)NH—$C_2$-$C_2$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_2$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —SO$_2$NH$_2$, —SO$_2$NH—$C_1$-$C_{12}$-alkyl, —SO$_2$NH—$C_2$-$C_{12}$-alkenyl, —SO$_2$NH—$C_2$-$C_{12}$-alkenyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_2$-alkenyl, —NHSO$_2$—$C_2$-$C_{12}$-alkenyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "heteroaryl," as used herein, refers to a mono-, bi-, or tri-cyclic aromatic radical or ring having from five to ten ring atoms of which one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "substituted heteroaryl," as used herein, refers to a heteroaryl group as previously defined, substituted by independent replacement of one, two, or three of the hydrogen atoms thereon with substituents including, but not limited to, —F, —Cl, —Br, —I, —OH, protected hydroxy, —NO$_2$, —CN, —$C_1$-$C_{12}$-alkyl optionally substituted with halogen, $C_2$-$C_{12}$-alkenyl optionally substituted with halogen, —C₂-C₁₂-alkynyl optionally substituted with halogen, —NH₂, protected amino, —NH—C₁-C₁₂-alkyl, —NH—C₂-C₁₂-alkenyl, —NH—C₂-C₁₂-alkenyl, —NH—C₃-C₁₂-cycloalkyl, —NH-aryl, —NH-heteroaryl, —NH-heterocycloalkyl, -dialkylamino, -diarylamino, -diheteroarylamino, —O—C₁-C₁₂-alkyl, —O—C₂-C₁₂-alkenyl, —O—C₂-C₁₂-alkenyl, —O—C₃-C₁₂-cycloalkyl, —O-aryl, —O-heteroaryl, —O-heterocycloalkyl, —C(O)—C₁-C₁₂-alkyl, —C(O)—C₂-C₁₂-alkenyl, —C(O)—C₂-C₁₂-alkenyl, —C(O)—C₃-C₁₂-cycloalkyl, —C(O)-aryl, —C(O)-heteroaryl, —C(O)-heterocycloalkyl, —CONH₂, —CONH—C₁-C₁₂-alkyl, —CONH—C₂-C₁₂-alkenyl, —CONH—C₂-C₁₂-alkenyl, —CONH—C₃-C₁₂-cycloalkyl, —CONH-aryl, —CONH-heteroaryl, —CONH-heterocycloalkyl, —OCO₂—C₁-C₁₂-alkyl, —OCO₂—C₂-C₁₂-alkenyl, —OCO₂—C₂-C₁₂-alkenyl, —OCO₂—C₃-C₁₂-cycloalkyl, —OCO₂-aryl, —OCO₂-heteroaryl, —OCO₂-heterocycloalkyl, —OCONH₂, —OCONH—C₁-C₁₂-alkyl, —OCONH—C₂-C₁₂-alkenyl, —OCONH—C₂-C₁₂-alkenyl, —OCONH—C₃-C₁₂-cycloalkyl, —OCONH-aryl, —OCONH-heteroaryl, —OCONH-heterocycloalkyl, —NHC(O)—C₁-C₁₂-alkyl, —NHC(O)—C₂-C₁₂-alkenyl, —NHC(O)—C₂-C₁₂-alkenyl, —NHC(O)—C₃-C₁₂-cycloalkyl, —NHC(O)-aryl, —NHC(O)-heteroaryl, —NHC(O)-heterocycloalkyl, —NHCO₂—C₁-C₁₂-alkyl, —NHCO₂—C₂-C₁₂-alkenyl, —NHCO₂—C₂-C₁₂-alkenyl, —NHCO₂—C₃-C₁₂-cycloalkyl, —NHCO₂-aryl, —NHCO₂-heteroaryl, —NHCO₂-heterocycloalkyl, —NHC(O)NH₂, NHC(O)NH—C₁-C₁₂-alkyl, —NHC(O)NH—C₂-C₁₂-alkenyl, —NHC(O)NH—C₂-C₁₂-alkenyl, —NHC(O)NH—C₃-C₂-cycloalkyl, —NHC(O)NH-aryl, —NHC(O)NH-heteroaryl, —NHC(O)NH-heterocycloalkyl, NHC(S)NH₂, NHC(S)NH—C₁-C₁₂-alkyl, —NHC(S)NH—C₂-C₁₂-alkenyl, —NHC(S)NH—C₂-C₁₂-alkenyl, —NHC(S)NH—C₃-C₂-cycloalkyl, —NHC(S)NH-aryl, —NHC(S)NH-heteroaryl, —NHC(S)NH-heterocycloalkyl, —NHC(NH)NH₂, NHC(NH)NH—C₁-C₁₂-alkyl, —NHC(NH)NH—C₂-C₁₂-alkenyl, —NHC(NH)NH—C₂-C₁₂-alkenyl, —NHC(NH)NH—C₃-C₁₂-cycloalkyl, —NHC(NH)NH-aryl, —NHC(NH)NH-heteroaryl, —NHC(NH)NH-heterocycloalkyl, NHC(NH)—C₁-C₁₂-alkyl, —NHC(NH)—C₂-C₁₂-alkenyl, —NHC(NH)-C₂-C₁₂-alkenyl, —NHC(NH)—C₃-C₁₂-cycloalkyl, —NHC(NH)-aryl, —NHC(NH)-heteroaryl, —NHC(NH)-heterocycloalkyl, —C(NH)NH—C₁-C₁₂-alkyl, —C(NH)NH—C₂-C₁₂-alkenyl, —C(NH)NH—C₂-C₁₂-alkenyl, —C(NH)NH—C₃-C₁₂-cycloalkyl, —C(NH)NH-aryl, —C(NH)NH-heteroaryl, —C(NH)NH-heterocycloalkyl, —S(O)—C₁-C₁₂-alkyl, —S(O)—C₂-C₁₂-alkenyl, —S(O)—C₂-C₁₂-alkenyl, —S(O)—C₃-C₁₂-cycloalkyl, —S(O)-aryl, —S(O)-heteroaryl, —S(O)-heterocycloalkyl —SO₂NH₂, —SO₂NH—C₁-C₁₂-alkyl, —SO₂NH—C₂-C₁₂-alkenyl, —SO₂NH—C₂-C₁₂-alkenyl, —SO₂NH—C₃-C₁₂-cycloalkyl, —SO₂NH-aryl, —SO₂NH-heteroaryl, —SO₂NH-heterocycloalkyl, —NHSO₂—C₁-C₁₂-alkyl, —NHSO₂—C₂-C₁₂-alkenyl, —NHSO₂—C₂-C₁₂-alkenyl, —NHSO₂—C₃-C₁₂-cycloalkyl, —NHSO₂-aryl, —NHSO₂-heteroaryl, —NHSO₂-heterocycloalkyl, —CH₂NH₂, —CH₂SO₂CH₃, -aryl, -arylalkyl, -heteroaryl, -heteroarylalkyl, -heterocycloalkyl, —C₃-C₁₂-cycloalkyl, -methoxymethoxy, -methoxyethoxy, —SH, —S—C₁-C₁₂-alkyl, —S—C₂-C₁₂-alkenyl, —S—C₂-C₁₂-alkenyl, —S—C₃-C₁₂-cycloalkyl, —S-aryl, —S-heteroaryl, —S-heterocycloalkyl, or methylthiomethyl.

The term "C₃-C₁₂-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl.

The term "substituted C₃-C₁₂-cycloalkyl," as used herein, refers to a C₃-C₁₂-cycloalkyl group as previously defined, substituted by independent replacement of one, two, or three of the hydrogen atoms thereon with substituents including, but not limited to, —F, —Cl, —Br, —I, —OH, protected hydroxy, —NO₂, —CN, —C₁-C₁₂-alkyl optionally substituted with halogen, C₂-C₁₂-alkenyl optionally substituted with halogen, —C₂-C₁₂-alkynyl optionally substituted with halogen, —NH₂, protected amino, —NH—C₁-C₁₂-alkyl, —NH—C₂-C₁₂-alkenyl, —NH—C₂-C₁₂-alkenyl, —NH—C₃-C₁₂-cycloalkyl, —NH-aryl, —NH-heteroaryl, —NH-heterocycloalkyl, -dialkylamino, -diarylamino, -diheteroarylamino, —O—C₁-C₁₂-alkyl, —O—C₂-C₁₂-alkenyl, —O—C₂-C₁₂-alkenyl, —O—C₃-C₂-cycloalkyl, —O-aryl, —O-heteroaryl, —O-heterocycloalkyl, —C(O)—C₁-C₁₂-alkyl, —C(O)—C₂-C₁₂-alkenyl, —C(O)—C₂-C₁₂-alkenyl, —C(O)—C₃-C₁₂-cycloalkyl, —C(O)-aryl, —C(O)-heteroaryl, —C(O)-heterocycloalkyl, —CONH₂, —CONH—C₁-C₁₂-alkyl, —CONH—C₂-C₁₂-alkenyl, —CONH—C₂-C₁₂-alkenyl, —CONH—C₃-C₁₂-cycloalkyl, —CONH-aryl, —CONH-heteroaryl, —CONH-heterocycloalkyl, —OCO₂—C₁-C₁₂-alkyl, —OCO₂—C₂-C₁₂-alkenyl, —OCO₂—C₂-C₁₂-alkenyl, —OCO₂—C₃-C₁₂-cycloalkyl, —OCO₂-aryl, —OCO₂-heteroaryl, —OCO₂-heterocycloalkyl, —OCONH₂, —OCONH—C₁-C₁₂-alkyl, —OCONH—C₂-C₁₂-alkenyl, —OCONH—C₂-C₁₂-alkenyl, —OCONH—C₃-C₁₂-cycloalkyl, —OCONH-aryl, —OCONH-heteroaryl, —OCONH-heterocycloalkyl, —NHC(O)—C₁-C₁₂-alkyl, —NHC(O)—C₂-C₁₂-alkenyl, —NHC(O)—C₂-C₁₂-alkenyl, —NHC(O)—C₃-C₁₂-cycloalkyl, —NHC(O)-aryl, —NHC(O)-heteroaryl, —NHC(O)-heterocycloalkyl, —NHCO₂—C₁-C₁₂-alkyl, —NHCO₂—C₂-C₁₂-alkenyl, —NHCO₂—C₂-C₁₂-alkenyl, —NHCO₂—C₃-C₁₂-cycloalkyl, —NHCO₂-aryl, —NHCO₂-heteroaryl, —NHCO₂-heterocycloalkyl, —NHC(O)NH₂, NHC(O)NH—C₁-C₁₂-alkyl, —NHC(O)NH—C₂-C₁₂-alkenyl, —NHC(O)NH—C₂-C₁₂-alkenyl, —NHC(O)NH—C₃-C₁₂-cycloalkyl, —NHC(O)NH-aryl, —NHC(O)NH-heteroaryl, —NHC(O)NH-heterocycloalkyl, NHC(S)NH₂, NHC(S)NH—C₁-C₁₂-alkyl, —NHC(S)NH—C₂-C₁₂-alkenyl, —NHC(S)NH—C₂-C₁₂-alkenyl, —NHC(S)NH—C₃-C₁₂-cycloalkyl, —NHC(S)NH-aryl, —NHC(S)NH-heteroaryl, —NHC(S)NH-heterocycloalkyl, —NHC(NH)NH₂, NHC(NH)NH—C₁-C₁₂-alkyl, —NHC(NH)NH—C₂-C₁₂-alkenyl, —NHC(NH)NH—C₂-C₁₂-alkenyl, —NHC(NH)NH—C₃-C₁₂-cycloalkyl, —NHC(NH)NH-aryl, —NHC(NH)NH-heteroaryl, —NHC(NH)NH-heterocycloalkyl, NHC(NH)—C₁-C₁₂-alkyl, —NHC(NH)—C₂-C₁₂-alkenyl, —NHC(H)—C₂-C₂-alkenyl, —NHC(NH)—C₃-C₁₂-cycloalkyl, —NHC(NH)-aryl, —NHC(NH)-heteroaryl, —NHC(NH)-heterocycloalkyl, —C(NH)NH—C₁-C₁₂-alkyl, —C(H)NH—C₂-C₂-alkenyl, —C(NH)NH—C₂-C₁₂-alkenyl, —C(NH)NH—C₃-C₁₂-cycloalkyl, —C(NH)NH-aryl, —C(NH)NH-heteroaryl, —C(NH)NH-heterocycloalkyl, —S(O)—C₁-C₁₂-alkyl, —S(O)—C₂-C₁₂-alkenyl, —S(O)—C₂-C₁₂-alkenyl, —S(O)—C₃-C₁₂-cycloalkyl, —S(O)-aryl, —S(O)-heteroaryl, —S(O)-heterocycloalkyl —SO₂NH₂, —SO₂NH—C₁-C₁₂-alkyl, —SO₂NH—C₂-C₁₂-alkenyl, —SO₂NH—C₂-C₁₂-alkenyl, —SO₂NH—C₃-C₁₂-cycloalkyl, —SO₂NH-aryl, —SO₂NH-heteroaryl, —SO₂NH-heterocycloalkyl, —NHSO₂—C₁-C₁₂-alkyl, —NHSO₂—C₂-C₁₂-alkenyl, —NHSO₂—C₂-C₁₂-alkenyl, —NHSO₂—C₃-C₁₂-cycloalkyl, —NHSO₂-aryl, —NHSO₂-heteroaryl, —NHSO₂-heterocycloalkyl, —CH₂NH₂, —CH₂SO₂CH₃, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "$C_3$-$C_{12}$-cycloalkenyl," as used herein, denotes a monocyclic or bicyclic carbocyclic ring compound where each 5-membered ring has 0 to 1 double bonds and each 6-membered ring has 0 to 2 double bonds. Examples include, but not limited to, cyclopentenyl, cyclohexenyl, bicyclo [2.2.1] heptenyl, and bicyclo [2.2.2] octenyl.

The term "heterocycloalkyl," as used herein, refers to a non-aromatic 5-, 6- or 7-membered ring or a bi- or tri-cyclic group fused system, where (i) each ring contains carbon atoms and between one and three heteroatoms independently selected from oxygen, sulfur and nitrogen, as ring members (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (v) any of the above rings may be fused to a benzene ring. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group, as previously defined, substituted by independent replacement of one, two, or three of the hydrogen atoms thereon with substituents including, but not limited to, —F, —Cl, —Br, —I, —OH, protected hydroxy, —$NO_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NECO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C—(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkenyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_2$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "heteroarylalkyl," as used herein, refers to a $C_1$-$C_3$ alkyl or $C_1$-$C_6$ alkyl residue substituted with a heteroaryl ring. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three of the hydrogen atoms thereon with substituents including, but not limited to, —F, —Cl, —Br, —I, —OH, protected hydroxy, —$NO_2$, —CN, —$C_1$-$C_{12}$-alkyl optionally substituted with halogen, $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$alkenyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, NHC(S)NH—$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_2$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl.

The term "$C_1$-$C_6$ alkoxy," as used herein, refers to a $C_1$-$C_6$ alkyl group, as previously defined, attached to the parent molecular moiety through an oxygen atom. Examples of $C_1$-$C_6$-alkoxy include, but are not limited to, methoxy, ethoxy, propoxy, isopropoxy, n-butoxy, tert-butoxy, neopentoxy and n-hexoxy.

The term "$C_1$-$C_3$-alkyl-amino," as used herein, refers to one or two $C_1$-$C_3$-alkyl groups, as previously defined, attached to the parent molecular moiety through a nitrogen atom. Examples of $C_1$-$C_3$-alkyl-amino include, but are not limited to, methylamino, dimethylamino, ethylamino, diethylamino, and propylamino.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl) ($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$ alkyl), —C(O)$NH_2$, and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxy protecting groups include, but are not limited to, acyl, methylthiomethyl, tert-butyl-dimethylsilyl, tert-butyldiphenylsilyl, acyl substituted with an aromatic group and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999).

Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

"An effective amount," as used herein, refers to an amount of a compound which confers a therapeutic effect on the treated subject. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Provide as used herein, means either directly administering a compound or composition of the present invention, or administering a pharmaceutically acceptable ester, prodrug, salt, derivative or analog of a compound of Formula I which will form an equivalent amount of the active compound or substance within the body.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope fo sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen.

The additional agents may be administered separately, as part of a multiple dose regimen, from the compounds of this invention. Alternatively, those agents may be part of a single dosage form, mixed together with the compounds of this invention in a single composition.

As used herein, unless otherwise indicated, the term "bacterial infection(s)" or "protozoa infections"; includes, but is not limited to, bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections and disorders related to such infections include, but are not limited to, the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or *Peptostreptococcus* spp. *Pseudomonas* spp.; pharynigitis, rheumatic fever, and glomerulonephritis related to infection by *Streptococcus pyogenes*, Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *S. pyogenes, S. agalactiae,* Streptococcal groups C-F (minute-colony streptococci), viridans streptococci, *Corynebacterium* spp., *Clostridium* spp., or *Bartonella henselae*; uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum,* or *Nesseria gonorrheae*; toxin diseases related to infection by *S. aureus* (food poisoning and Toxic shock syndrome), or Groups A, S. and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp. odontogenic infection related to infection by viridans streptococci; persistent cough related to infection by *Bordetella pertussis*; gas gangrene related to infection by *Clostridium perfringens* or *Bacteroides* spp.; Skin infection by *S. aureus, Propionibacterium* acne; atherosclerosis related to infection by *Helicobacter pylori* or *Chlamydia pneumoniae*; or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis,* or *Bordetella* spp.; cow enteric disease related to infection by *E. coli* or protozoa (i.e., coccidia, cryptosporidia, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae, P. multocida*, or *Mycoplasma* spp.; swine enteric disease related to infection by *E. coli, Lawsonia intracellularis, Salmonella* spp., or *Serpulina hyodyisinteriae*; cow footrot related to infection by *Fusobacterium* spp.; cow metritis related to infection by *E. coli*; cow hairy warts related to Infection by *Fusobacterium necrophorum* or *Bacteroides nodosus*; cow pink-eye related to infection by *Moraxella bovis*, cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. *Staphylococcus* or *P. multocida*; and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al.,"The Sanford Guide To Antimicrobial Therapy," 26th Edition, (Antimicrobial Therapy, Inc., 1996).

Antibacterial Activity

It will be appreciated by one of ordinary skill in the art that the compounds of the present invention are expected to be useful as broad spectrum antibacterial agents against bacterial infections, as defined herein, in humans, other mammals, and fish. The compounds of Formula I are expected to overcome a wide array of macrolide-resistant strains of bacteria because of their novel structure. The compounds of the present invention are particularly expected to have antibacterial activity against *S. aureus, S. epidermidis, S. pneumoniae, S. pyogenes*, enterococci, *Moraxella catarrhalis* and *H influenzae*.

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 µg/ml to about 0.03 µg/ml. The diluted compounds (2 µl/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 µl/well of adjusted bacterial inoculum. The 96 well plates were covered and incubated at 35 +/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC.

The compounds of the invention generally demonstrated an MIC in the range from about 64 µg/ml to about 0.03 µg/ml.

All in vitro testing follows the guidelines described in the Approved Standards M7-A4 protocol, published by the National Committee for Clinical Laboratory Standards (NC-CLS).

Pharmaceutical Compositions.

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result.

By a "therapeutically effective amount" of a compound of the invention is meant a sufficient amount of the compound to treat or prevent bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Abbreviations

Abbreviations which may appear in the following synthetic schemes and examples are:

Ac for acetyl;
AIBN for azobisisobutyronitrile;
9-BBN for 9-borabicyclo[3.3.1]nonane;
Boc for tert-butoxycarbonyl;
$Bu_3SnH$ for tributyltin hydride;
Bz for benzyl;
CDI for carbonyldiimidazole;
dba for dibenzylidene acetone;
DBU for 1,8-diazabicyclo[5.4.0]undec-7-ene;
DEAD for diethylazodicarboxylate;
Dess-Martin periodinane for 1,1,1-tris(acetyloxy)-1,1-dihydro-1,2-benziodoxol-3-(1H)-one;
DMAP for dimethylaminopyridine;
DMF for dimethyl formamide;
DMSO for dimethyl sulfoxide;
DPPA for diphenylphosphoryl azide;
dppb for diphenylphosphino butane;
EtOAc for ethyl acetate;
iPrOH for isopropanol;
NaHMDS for sodium bis(trimethylsilyl)amide;
NMO for N-methylmorpholine N-oxide;
MeOH for methanol;
MOM for methoxymethyl;
PDC for pyridinium dichromate;
Ph for phenyl;
POPd for dihydrogen dichlorobis(di-tert-butylphosphino) palladium(II);
TBAHS for tetrabutyl ammonium hydrogen sulfate;
TBS for tert-butyl dimethylsilyl;
TEA for triethylamine;
TES for triethyl silyl;
THF for tetrahydrofuran;
TMS for trimethyl silyl;
TPAP for tetra-n-propyl ammonium perruthenate;
TPP for triphenylphosphine; and
Tris for Tris(hydroxymethyl)aminomethane.

Synthetic Methods

The compounds and processes of the present invention will be better understood in view of the following synthetic schemes that illustrate the methods by which the compounds of the invention may be prepared.

A preferred intermediate for the preparation of compounds represented by formula I is a compound represented by the formula Ia:

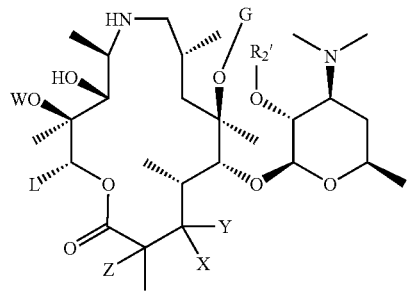

(Ia)

wherein
1) X is hydrogen;
2) Y is

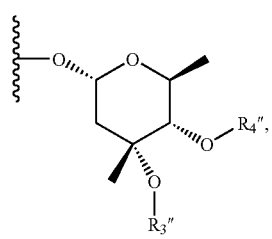

where $R_3''$ and $R_4''$ are as previously defined; and
3) G, L, W, Z, and $R_2'$ are as previously defined.

Preferred intermediate of formula 1a, where G is not hydrogen may be produced via methods described in Or et al., International Publication No. WO 01/14397, which discloses 6-O-substituted azithromycin derivatives.

A second preferred intermediate for the preparation of compounds represented by formula I is a compound represented by the formula Ib

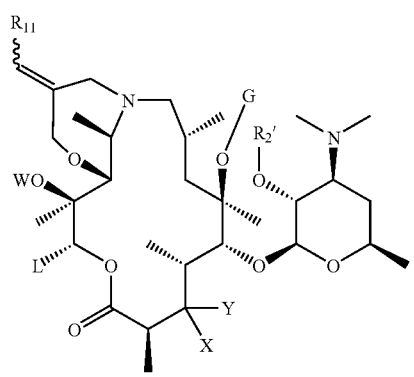

(Ib)

wherein G, L, W, X, Y, $R_{11}$, and $R_2'$ are as previously defined.

A third preferred intermediate for the preparation of compounds represented by formula I is a compound represented by the formula Ic

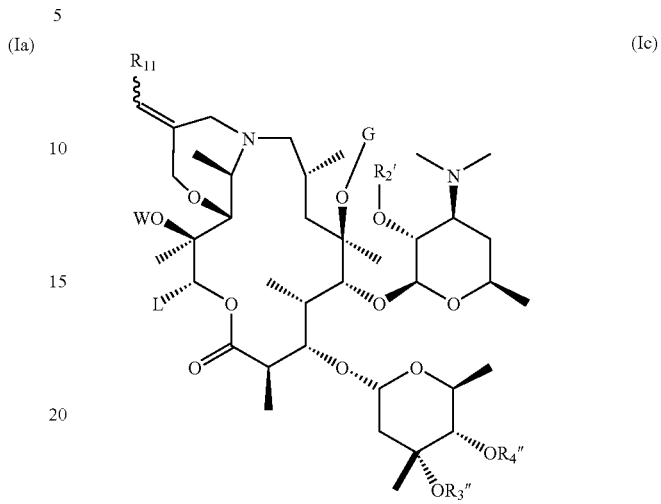

(Ic)

wherein G, L, W, $R_{11}$, and $R_2'$ are as previously defined.

A fourth preferred intermediate for the preparation of compounds represented by formula I is a compound represented by the formula Id:

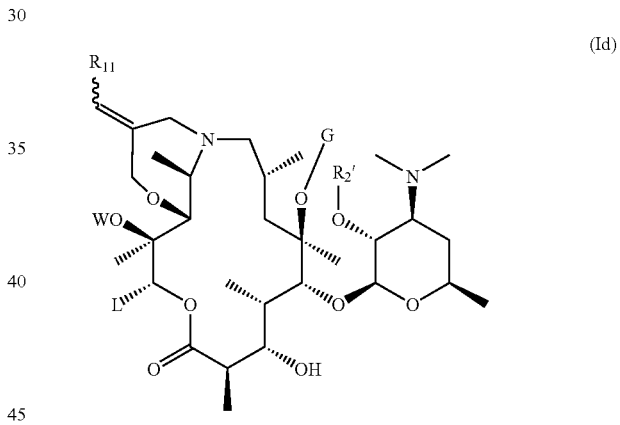

(Id)

wherein G, L, W, $R_{11}$, and $R_2'$ are as previously defined.

A fifth preferred intermediate for the preparation of compounds represented by formula I is a compound represented by the formula Ie:

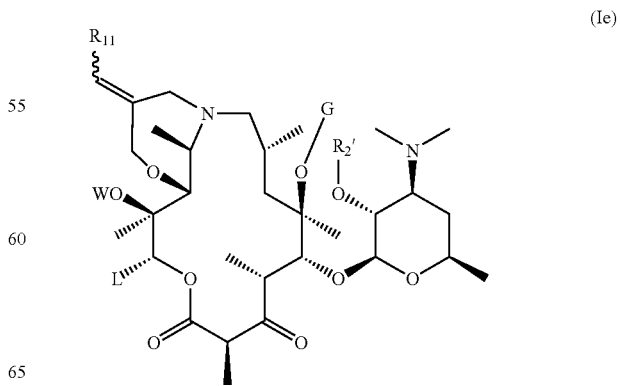

(Ie)

wherein G, L, W, $R_{11}$, and $R_2'$ are as previously defined.

Scheme 1

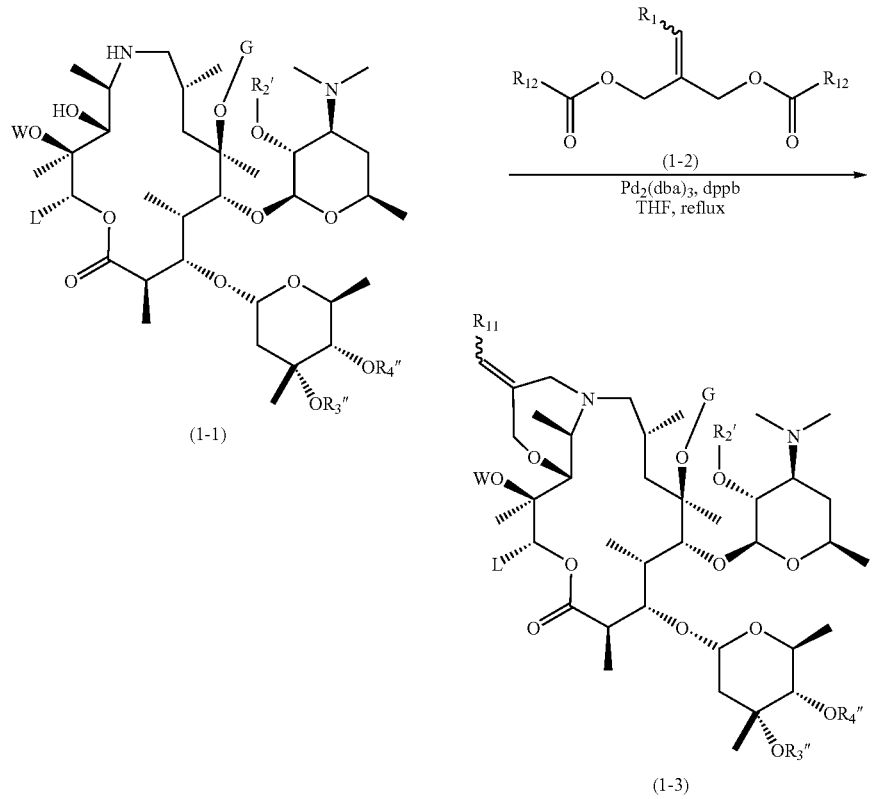

Desmethyl azithromycin of formula (1-1), where G, L, W, $R_2'$, $R_3''$, and $R_4''$ are as previously defined, is reacted with an alkylating agent of the formula (1-2): $R_{12}$—C(O)O—$CH_2[C$=$CHR_{11}]CH_2$—OC(O)—$R_{12}$, wherein $R_{11}$ ss as previously defined and $R_{12}$ is —$R_{11}$ or —$OR_{11}$, where $R_1$ is as previously defined.

Most palladium (0) catalysts are expected to produce compounds of formula (1-3). Some palladium (II) catalysts, such as palladium (II) acetate, which are converted into a palladium (0) species in-situ by the actions of a phosphine, will work as well. See, for example, Beller et al. *Angew. Chem. Int. Ed. Engl.,* 1995, 34 (17), 1848. The palladium catalyst can be selected from, but not limited to, palladium (II) acetate, tetrakis(triphenylphospine)palladium (0), tris(dibenzylideneacetone)dipalladium, tetradibenzylideneacetone)dipalladium and the like. Palladium on carbon and palladium (II) halide catalysts are less preferred than other palladium catalysts for this process. Suitable phosphines include, but are not limited to, triphenylphosphine, bis(diphenylphosphino)methane, bis(diphenylphosphino)ethane, bis(diphenylphosphino)propane, 1,4-bis(diphenylphosphino)butane, bis(diphenylphosphino)pentane, and tri-o-tolyl-phosphine, and the like.

The reaction is carried out in an aprotic solvent, at a temperature range of 25° C.-100° C., preferably at elevated temperature, more preferably at or above 50° C. to 80° C. Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran or toluene. The reaction can also be carried out optionally in the presence of an organic acid including, but not limited to, acetic acid, propionic acid, and the like.

Generally, the alkylating agents have the formula (1-2) as previously described. The preferred alkylating agents are those wherein $R_{12}$ is tert-butyl, isopropyl or isobutyl. The alkylating reagents are prepared by reaction of a diol with a wide variety of compounds for incorporating the di-carbonate moiety. The compounds include, but are not limited to, tert-butyl chloroformate, di-tert-butyl dicarbonate, and 1-(tert-butoxycarbonyl)imidazole and the reaction is carried out in the presence of an organic or an inorganic base. The temperature of the reaction varies from about −30° C. to approximately 30° C. Preferably the alkylating reagent is di-tert-butyl dicarbonate.

An alternative method of converting the alcohol into the carbonate involves treating the alcohol with phosgene or triphosgene to prepare the chloroformate derivative of the diol. The di-chloroformate derivative is then converted into the di-carbonate by the methods described in Cotarca, L., Delogu, P., Nardelli, A., Sunijic, V, *Synthesis,* 1996, 553. The reaction can be carried out in a variety of organic solvents such as dichloromethane, toluene, diethyl ether, ethyl acetate and chloroform in the presence of a base. Examples of suitable bases include, but are not limited to, sodium hydroxide, potassium hydroxide, ammonium hydroxide, sodium carbonate, potassium carbonate, ammonium carbonate, DMAP, pyridine, triethylamine and the like. The temperature can vary from 0° C. to approximately 60° C. The reaction runs to completion in 3 to 5 hours.

Scheme 2

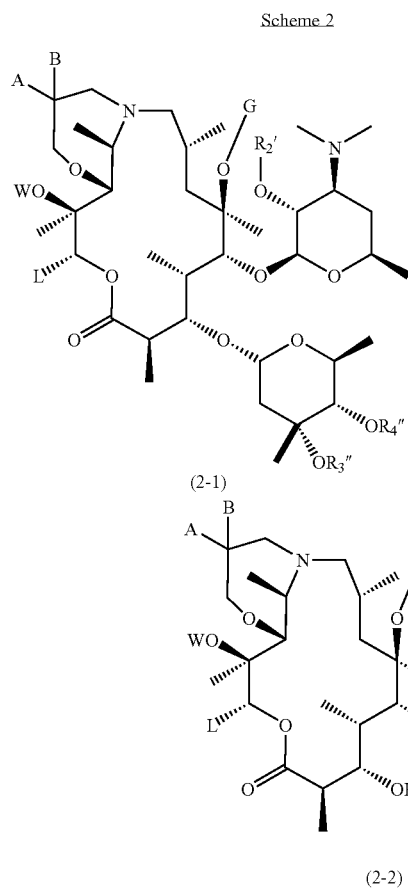

(2-1)

(2-2)

Another process of the invention involves the removal of the cladinose moiety of the compounds of formula (2-1), wherein A, B, G, L, W $R_2'$, $R_3''$, and $R_4''$ are as previously defined. The cladinose moiety of the macrolide compound (2-1) is removed either by mild acid hydrolysis or by enzymatic hydrolysis to afford compounds of formula (2-2) in Scheme 2. Representative acids include, but are not limited to, dilute hydrochloric acid, sulfuric acid, perchloric acid, chloroacetic acid, dichloroacetic acid or trifluoroacetic acid. Suitable solvents for the reaction include, but are not limited to, methanol, ethanol, isopropanol, butanol, water and mixtures there of. Reaction times are typically 0.5 to 24 hours. The reaction temperature is preferably 0 to 80° C.

Scheme 3

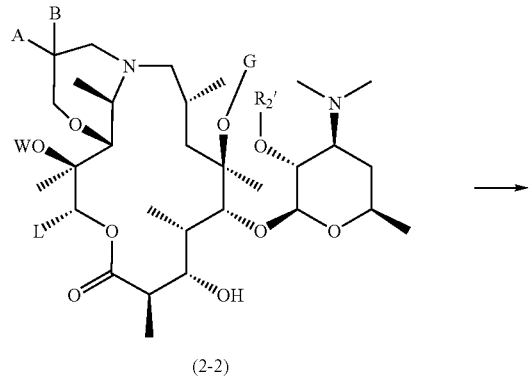

(2-2)

-continued

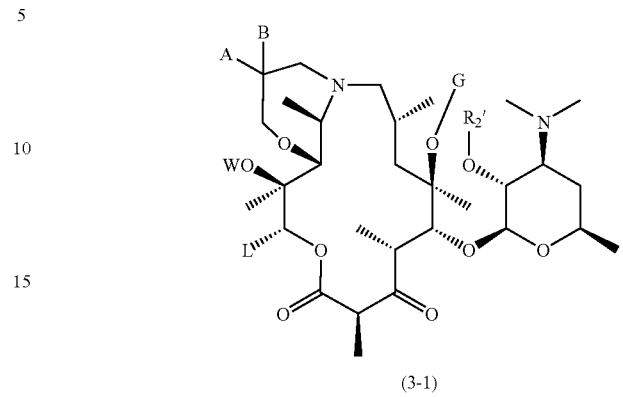

(3-1)

Conversion of compounds of formula (2-2) to compounds of formula (3-1) can be accomplished by oxidation of the 3-hydroxy group to a 3-oxo group using Dess-Martin periodinane (for further details concerning the Dess-Martin oxidation see D. B. Dess, J. C. Martin, *J. Org. Chem.* 48, 4155 (1983)), a Corey-Kim reaction with N-chlorosuccinimide-dimethylsulfide (for further details concerning the Corey-Kim oxidation reaction see E. J. Corey, C. U. Kim, *J. Am. Chem. Soc.* 94, 7586 (1972)), or a Moffat oxidation with a carbodiimide-DMSO complex in the presence of pyridinium trifluoroacetate, TPAP, PDC, and the like (for further details concerning the Moffat oxidation see J. G. Moffatt, "Sulfoxide-Carbodiimide and Related Oxidations" in *Oxidation* vol. 2, R. L. Augustine, D. J. Trecker, Eds. (Dekker, New York, 1971) pp 1-64; T. T. Tidwell, *Org. React.* 39, 297-572 passim (1990); and T. V. Lee, *Comp. Org. Syn.* 7, 291-303 passim (1991)). In a preferred embodiment, compounds of formula (4-1) are treated with Dess-Martin periodinane in dichloromethane at about 0° C. to about 25° C. for approximately 0.5 to 4 hours to produce compounds of formula (5-1).

Scheme 4

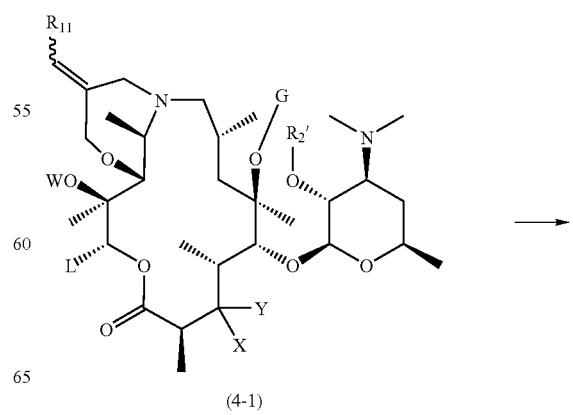

(4-1)

-continued

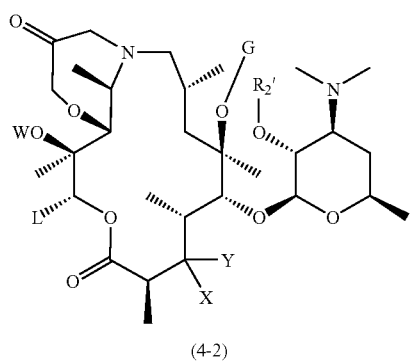

(4-2)

Scheme 4 illustrates another process of the invention by which to prepare compound of the present invention. Conversion of alkenes (4-1) into ketones (4-2) can be accomplished by ozonolysis followed by decomposition of the ozonide with the appropriate reducing agents. The reaction is typically carried out in an inert solvent such as, but not limited to, methanol, ethanol, ethyl acetate, glacial acetic acid, chloroform, methylene chloride or hexane or mixtures thereof, preferably methanol, preferably at −78° C. to −20° C. Representative reducing agents are, for example, triphenylphosphine, trimethylphosphite, thiourea, and dimethyl sulfide, preferably triphenylphosphine. A more thorough discussion of ozonolysis and conditions therefor may be found in J. March, *Advanced Organic Chemistry*, $4^{th}$ ed., Wiley & Son, Inc, 1992. Alternatively, compounds of formula (4-2) can be prepared from compounds of formula (4-1) dihydroxydation with $OsO_4$ followed by $NaIO_4$ cleavage.

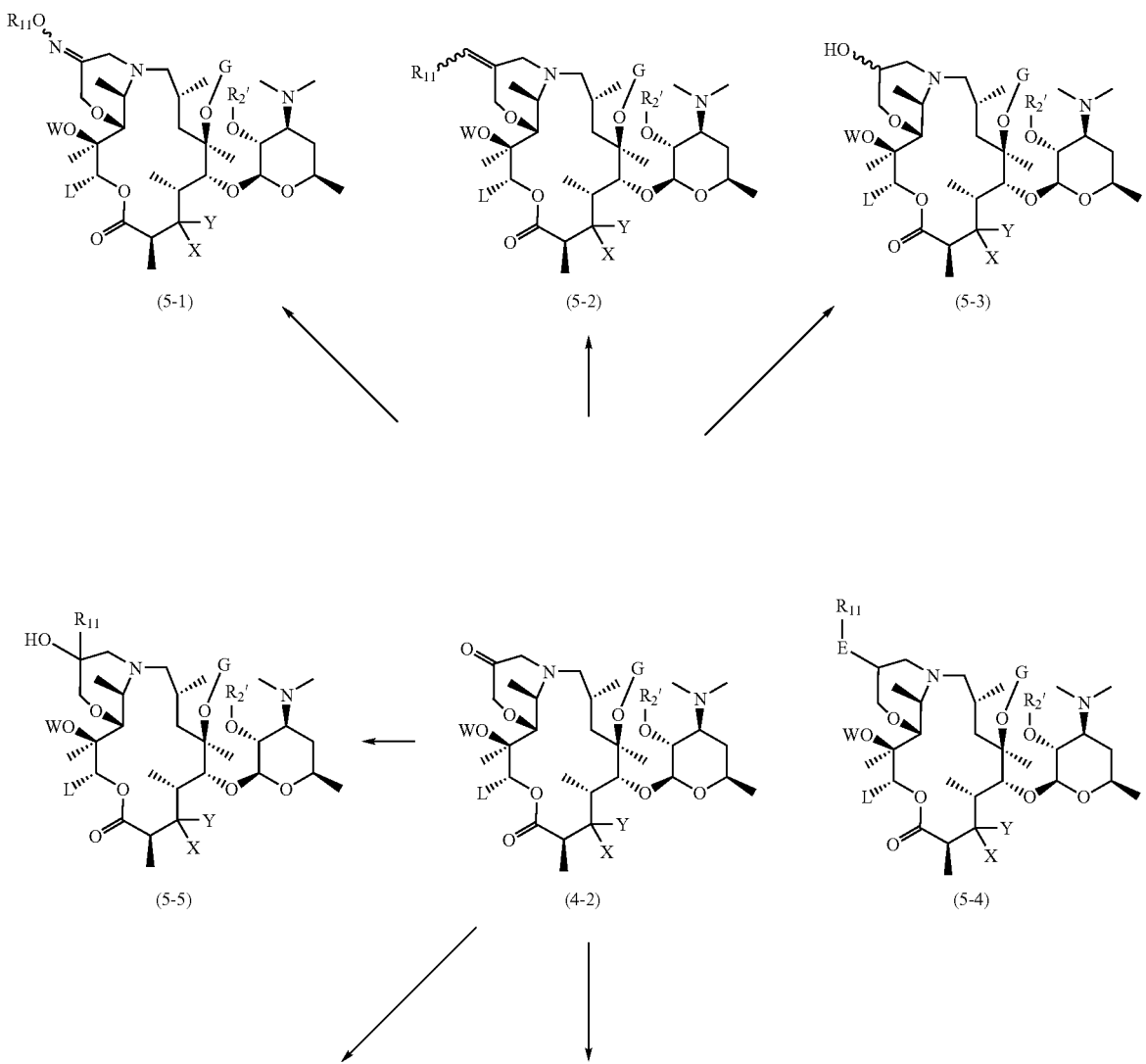

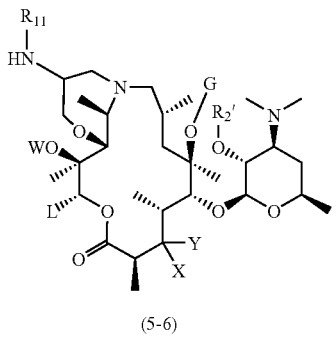 (5-6)

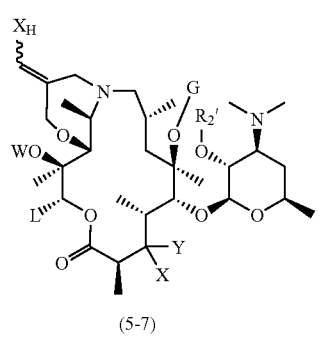 (5-7)

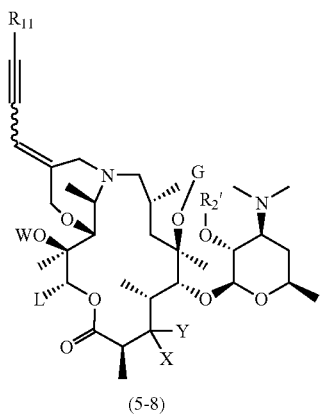 (5-8)

Compounds according to the invention of the formula (4-2) can be further functionalized in a variety of ways. Scheme 5 details a procedure for the conversion of the ketone of formula (4-2) into an oxime of formula (5-1). Oxime formation can be accomplished using the appropriate substituted hydroxylamine under either acidic or basic conditions in a variety of solvents. Representative acids include, but are not limited to, hydrochloric, phosphoric, sulfuric, p-toluenesulfonic, and pyridinium p-toluene sulfonate. Likewise, representative bases include, but are not limited to, triethylamine, pyridine, diisopropylethyl amine, 2,6-lutidine, and the like. Appropriate solvents include, but are not limited to, methanol, ethanol, water, tetrahydrofuran, 1,2-dimethoxyethane, and ethyl acetate. Preferably the reaction is carried out in ethanol using triethylamine as the base. The reaction temperature is generally 25° C. and reaction time is 1 to 12 hours.

It will be appreciated by one skilled in the art that ketones of formula (4-2) can be transformed into alkenes of formula (5-2) and (5-7) via Wittig reaction with the appropriate phosphonium salt in the presence of a base, see (a) Burke, *Tetrahedron Lett.*, 1987, 4143-4146, (b) Rathke and Nowak, *J. Org. Chem.*, 1985, 2624-2626, (c) Maryanoff and Reitz, *Chem. Rev.*, 1989, 863-927. Furthermore, vinyl halides of formula (5-7) can be functionalized by Sonogashira coupling with alkynes in the presence of a palladium catalyst, a copper halide and an amine base to give compounds of formula (5-8) (see (a) Sonogashira, *Comprehensive Organic Synthesis*, Volume 3, Chapters 2,4; (b) Sonogashira, *Synthesis* 1977, 777.). In a similar manner, alkenes of formula (5-2) can be obtained from vinyl halides (5-7) via Suzuki cross coupling with organoboron reagents in the presence of a palladium catalyst and a base, or via Stille cross coupling with organostananes in the presence of a palladium catalyst (see (a) Suzuki, *J. Organomet. Chem.* 1999, 576,147-168, (b) Stille, *Angew. Chem. Int. Ed Engl.*, 1986, 508-524 (c) Farina, *J. Am. Chem. Soc.*, 1991, 9585-9595).

Furthermore, alcohols of type (5-3) can be prepared by reduction of the corresponding ketone of formula (4-2) under a variety of conditions (see Hudlicky, M. *Reductions in Organic Chemistry*, Ellis Horwood Limited: Chichester, 1984). The alcohols thus derived can be further modified to give compounds of formula (5-4). A process to generate compounds of formula (5-4) includes, but is not limited to, alkylation of the alcohol with an electrophile or conversion of the alcohol into a leaving group, such as a triflate, tosylate, phosponate, halide, or the like, followed by displacement with a heteroatom nucleophile (e.g. an amine, alkoxide, sulfide or the like).

Yet another means by which to functionalize ketones of formula (4-2) is via addition of Grignard reagents to form alcohols of formula (5-5). The requisite Grignard reagents are readily available via the reaction of a variety of alkyl or aryl halides with magnesium under standard conditions (see B. S. Furniss, A. J. Hannaford, P. W. G. Smith, A. R. Tatchell, *Vogel's Textbook of Practical Organic Chemistry*, $5^{th}$ ed., Longman, 1989). The addition is performed in an inert solvent, generally at low temperatures. Suitable solvents include, but are not limited to, tetrahydrofuran, diethylether, 1,4-dioxane, 1,2-dimethoxyethane, and hexanes. Preferably the solvent is tetrahydrofuran or diethylether. Preferably the reaction is run at −78° C. to 0° C.

In a similar way, reaction with other organometallic reagents gives rise to alcohols of formula (5-5). Examples of useful organometallic reagents include, but are not limited to, organo-aluminum, organo-lithium, organo-cerium, organo-zinc, organo-thallium, and organo-boron reagents. A more thorough discussion of organometallic reagents can be found in B. S. Furniss, A. J. Hannaford, P. W. G. Smith, A. R. Tatchell, *Vogel's Textbook of Practical Organic Chemistry*, $5^{th}$ ed., Longman, 1989.

Ketone of formula (4-2) can be further utilized by conversion into amine of formula (5-6) via a reductive amination. Reductive amination is achieved by treating the ketone with an amine in the presence of a reducing agent to obtain the product amine (5-6). The reaction can be carried out either with or without added acid. Examples of acids that are commonly used include, but are not limited to, hydrochloric, phosphoric, sulfuric, acetic, and the like. Reducing agents that effect reductive amination include, but are not limited to, hydrogen and a catalyst, zinc and hydrochloric acid, sodium cyanoborohydride, sodium borohydride, iron pentacarbonyl, and alcoholic potassium hydroxide. Generally alcoholic solvents are used. The preferred conditions use sodium cyanoborohydride in methanol with added acetic acid.

It will be appreciated by one skilled in the art, that the unsaturated compounds represented by compounds (5-2) and (5-8) can be reduced to form the corresponding saturated compound (see Hudlicky, M., *Reductions in Organic Chemistry*, Ellis Horwood Limited: Chichester, 1984).

Scheme 6

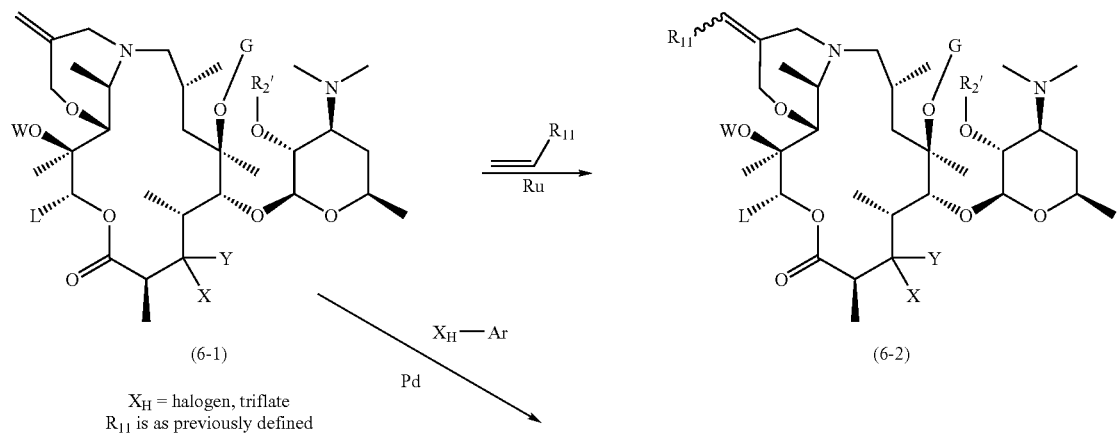

$X_H$ = halogen, triflate
$R_{11}$ is as previously defined

Compounds of the invention according to formula (6-1) are also capable of further functionalization to generate compounds of the present invention. Alkene (6-2) can be treated with an aryl halide or aryl triflate in the presence of a palladium catalyst [Pd(0) or Pd(II)] to provide compound (6-3): (See (a) Heck, *Palladium Reagents in Organic Synthesis*, Academic Press: New York, 1985, Chapter 1; (b) Sonogashira, *Comprehensive Organic Synthesis*, Volume 3, Chapters 2,4; (c) Sonogashira, *Synthesis* 1977, 777). Under the Heck coupling conditions, regioisomers and stereoisomers of the double bond are possible. Alternatively, compound (6-1) can undergo a cross metathesis reaction with vinylaromatic derivatives using ruthenium catalysts to give compounds of formula (6-2) (see (a) *J. Org. Chem.* 2000, 65, 2204-2207; (b) Reviews: *Synlett.* 1999, 2, 267; (c) Reviews: Ivin, K. J.; Mol, J. C., *Olefin Metathesis and Metathesis Polymerization*, $2^{nd}$ ed., Academic Press: New York, 1997; (d) *J. Org. Chem.* 1999, 64, 4798-4816; (e) *Angew. Chem.,* *Int. Ed. Engl.* 1997, 36, 2036-2056; (f) *Tetrahedron* 1998, 54, 4413-4450).

Scheme 7

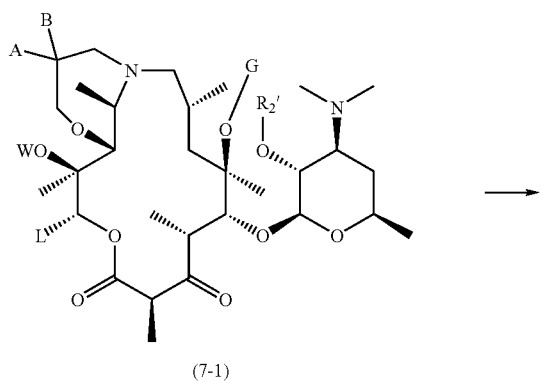

-continued

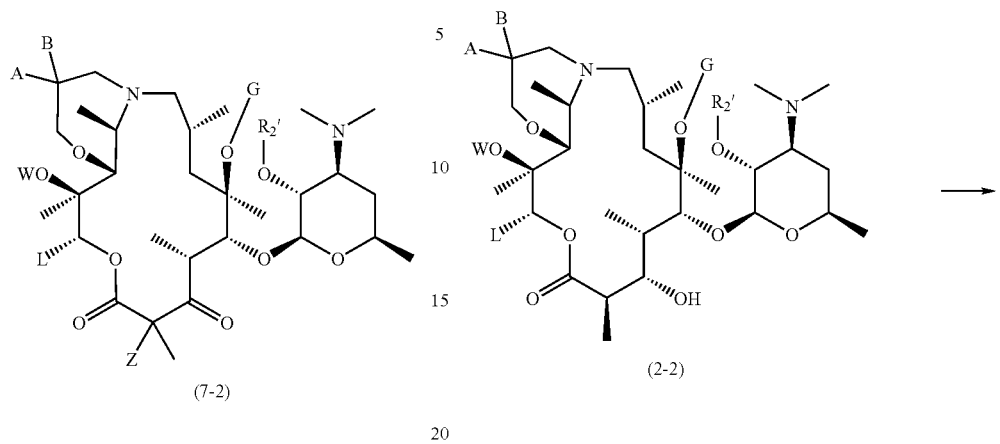

(7-2)

(2-2)

Scheme 8

Scheme 7 illustrates the procedure by which compounds of formula (7-1), wherein A, B, Q, and $R_2'$ are as previously defined, may be converted to compounds of formula (7-2), wherein A, B, Q, Z, and $R_2'$ are as previously defined, by treatment with a halogenating reagent. This reagent acts to replace a hydrogen atom with a halogen atom at the C-2 position of the ketolide. Various halogenating reagents may be suitable for this procedure.

Fluorinating reagents include, but are not limited to, N-fluorobenzenesulfonimide in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, N-fluoroperfluoropiperidine in the presence of base.

Chlorinating reagents include, but are not limited to, hexachloroethane in the presence of base, $CF_3CF_2CH_2ICl_2$, $SO_2Cl_2$, $SOCl_2$, $CF_3SO_2Cl$ in the presence of base, $Cl_2$, NaOCl in the presence of acetic acid.

Brominating reagents include, but are not limited to, $Br_2 \cdot pyridine \cdot HBr$, $Br_2$/acetic acid, N-bromosuccinimide in the presence of base, $LDA/BrCH_2CH_2Br$, or $LDA/CBr_4$.

A suitable iodinating reagent is N-Iodosuccinimide in the presence of base, or $I_2$, for example.

Suitable bases for the halogenating reactions requiring them are compounds such as alkali metal hydrides, such as NaH and KH, or amine bases, such as LDA or triethylamine, for example. Different reagents may require different type of base, but this is well known within the art.

A preferred halogenating reagent is N-fluorobenzenesulfonimide in the presence of sodium hydride.

Suitable solvents are dimethylformamide, dimethyl sulfoxide, pyrrolidinone and the like.

It will be appreciated by one skilled in the art that all ketolide compounds delineated herein may be halogenated at the 2-carbon if so desired.

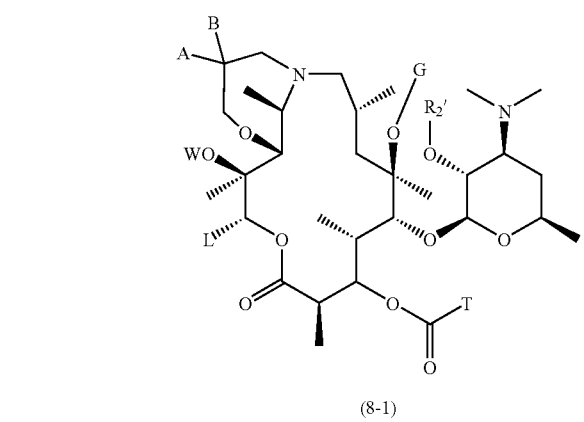

(8-1)

$T = R_{11}$, $NHR_{11}$, or $S(O)_nR_{11}$, where n and $R_{11}$ are as previously defined Scheme 8 illustrates a procedure for the acylation of the C-3 hydroxyl of compounds of formula (2-2). The hydroxyl group is acylated under basic conditions using a suitable acylating agent in an aprotic solvent. Typical acylating agents include, but are not limited to, acid chlorides, acid anhydrides, and chloroformates.

Typical bases include, but are not limited to, pyridine, triethylamine, diisopropyl ethylamine, N-methyl morpholine, N-methylpyrrolidine, 2,6-lutidine, 1,8-diazabicyclo[5.4.0]undec-7-ene. For a more extensive discourse on acylating conditions see for example, T. W. Greene and P. G. M. Wuts in "Protective Groups in Organic Synthesis" 3$^{rd}$ ed., John Wiley & Son, Inc, 1999, referred to above herein.

Scheme 9

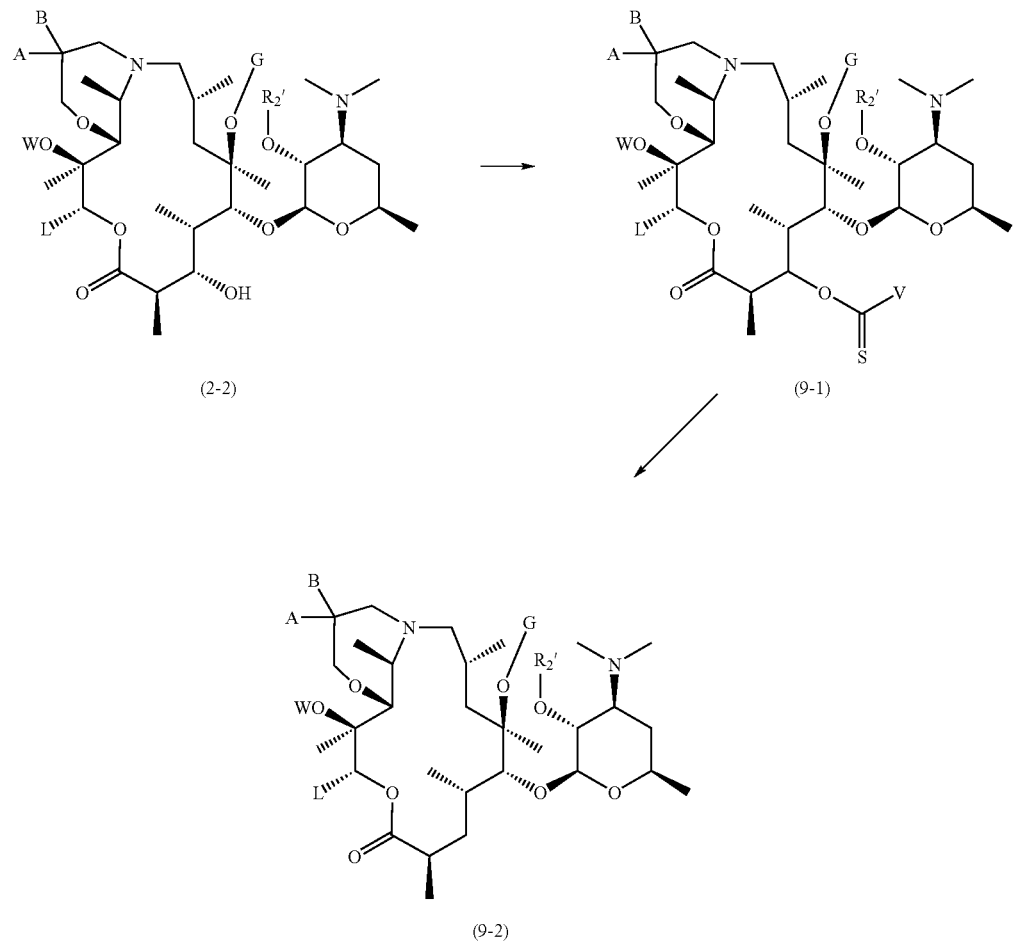

V = SR₁ or OR₁

Another process of the invention, as illustrated in Scheme 9, involves the C-3 deoxygenation of the macrolide (2-2) which can be accomplished via the two step procedure shown therein. In the first step the xanthate or thiocarbonate is formed by the reaction of alkoxide of alcohol (2-2) with the appropriate thiocarbonyl. For instance, formation of the xanthate can be accomplished by reaction of the alkoxide with either carbondisulfide followed by methyliodide, or a dithiocarbonyl imidazole; whereas the thiocarbonate can be prepared by the reaction of the alkoxide with either thiocarbonyldimidazole followed by methanol, ethanol or the like, or a thiochloroformate. One skilled in the art will appreciate that other reagents and conditions exist to perform these transformations and that the examples above are for illustrative purposes only and do not limit the scope of this invention. These reactions are typically run in a polar aprotic solvent, preferably tetrahydrofuran, acetonitrile, or N,N dimethylformamide.

In the second step of Scheme 9, the thiocarbonate or xanthate is decomposed to give the alkane. Most typically this is done under radical conditions using, for example, a silyl hydride such as (TMS)₃SiH, Ph₂SiH₂ or the like, a tin hydride such as Bu₃SnH, Ph₃SnH or the like, and a radical initiator such as AIBN or t-butyl peroxide. The preferred solvent is toluene.

Scheme 10

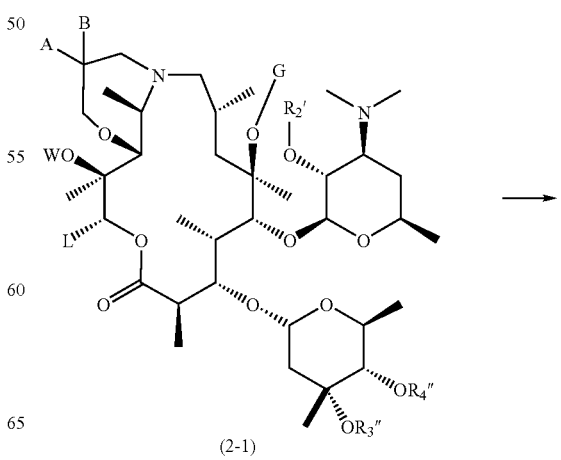

(2-1)

-continued

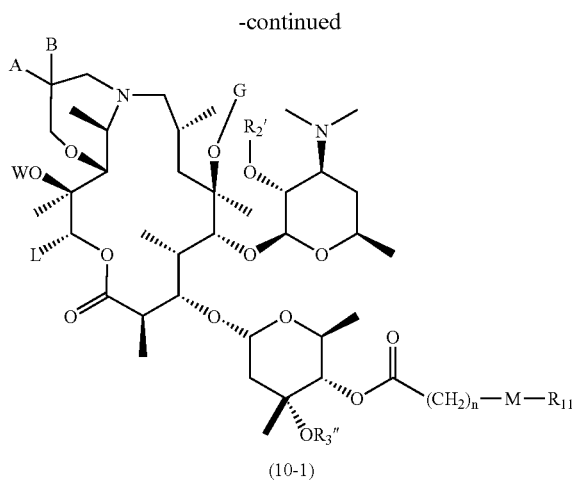

(10-1)

Acylation of the 4"-hydroxy of the cladinose ring of compounds may be achieved via similar methods by acylation of the 3-position hydroxy delineated in Scheme 8 to form compounds of formula (10-1), where n, M and $R_{11}$ are as previously defined. For further details concerning the acylation of the 4-hydroxy of the cladinose ring of compounds of formula (2-1), please see PCT Publication No. WO03/42228.

All references cited herein, whether in print, electronic, computer readable storage media or other form, are expressly incorporated by reference in their entirety, including but not limited to, abstracts, articles, journals, publications, texts, treatises, internet web sites, databases, patents, patent applications, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula II, wherein A and B Taken Together with the Carbon Atom to which They are Attached are C=$CH_2$, L is —$CH_2CH_3$, G=W=$R_2$'=$R_4$"=Hydrogen, and $R_3$" is —$CH_3$ Step 1a.

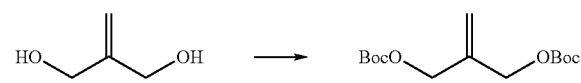

To a solution of 2-methylene-1,3-propane diol (5.28 g, 0.06 mmol) and di-tert-butyl dicarbonate (35 g, 0.16 mol) in 150 ml of dichloromethane is added 6N NaOH (70 ml) and TBAHS (3.4 g, 10 mmol). The mixture is stirred at room temperature overnight. The organic layer is separated, washed with $NaHCO_3$ (200 ml×3) and brine (200 ml), dried over anhydrous $MgSO_4$, and concentrated in vacuo to give the title compound.

$^1$H NMR ($CDCl_3$): δ 5.20(s, 2H); 4.44(s, 4H); 1.18(s, 18H). $^{13}$C NMR($CDCl_3$): δ 153.28, 138.50, 117.27, 82.27, 66.91, 27.83.

Step 1b.

To a solution of desmethyl azithromycin (14.7 g, 20 mmol), the compound from step 1a (6.92 g, 24 mmol) and dppb (512 mg, 1.2 mmol) in THF (200 ml), is added acetic acid (1.14, 20 mmol) and $Pd_2(dba)_3$ (550 mg, 0.5 mmol) under nitrogen. The mixture is refluxed for 4 hours, diluted with ethyl acetate (250 ml). washed with saturated $NaHCO_3$ (200 ml×2) and brine (200 ml), and dried over anhydrous $Na_2SO_4$. The solvent was removed in vacuo, and the residue was purified by flash chromatography ($SiO_2$, 2M $NH_3$ in methanol/$CH_2Cl_2$=5/95) to give the title compound (11 g).

MS (ESI) m/z 787.55 (M+H)$^+$ $^{13}$C NMR($CDCl_3$): δ 177.1, 145.6, 114.3, 103.2, 95.8, 84.4, 83.7, 79.6, 78.3, 77.2, 74.3, 74.2, 74.0, 73.2, 71.3, 69.6, 69.0, 66.0, 65.9, 64.5, 54.5, 53.7, 49.7, 45.4, 42.6, 41.2, 40.6, 35.4, 29.2, 27.2, 22.3, 21.9, 21.7, 21.2, 18.6, 16.7, 16.1, 11.1, 9.8, 7.6.

Example 2

Compound of Formula II, wherein A and B Taken Together with the Carbon Atom to which They are Attached are C=$CH_2$, L is —$CH_2CH_3$, G=W=$R_4$"=Hydrogen, $R_2$' is Ac, and $R_3$" is —$CH_3$ To a solution of compound from example 1 (0.85 g, 1.08 mmol) in $CH_2Cl_2$ (10 ml) was added acetic anhydride (1 ml) at room temperature. The mixture is stirred at room temperature for 1 hour, quenched by addition of saturated $NaHCO_3$ (10 ml). The organic phase is then separated and dried over anhydrous $Na_2SO_4$. The solvent is removed in vacuo, and the residue is purified via flash chromatography ($SiO_2$, hexane/acetone=1/1) to give the title compound (0.9 g).

MS (ESI) m/z 829.52 (M+H)$^+$. $^{13}$C NMR($CDCl_3$): δ 176.8, 170.3, 145.5, 114.3, 100.5, 95.8, 83.8, 83.7, 79.5, 78.1, 77.3, 74.4, 74.3, 74.0, 73.3, 71.8, 69.5, 68.1, 66.3, 64.5, 63.5, 54.6, 49.6, 45.3, 42.1, 40.5, 35.4, 30.9, 27.1, 22.3, 21.9, 21.8, 21.5, 21.4, 21.1, 18.6, 16.7, 16.2, 11.1, 9.7, 7.6.

Example 3

Compound of Formula II, wherein A is Hydrogen, B is —$CH_3$, L is —$CH_2CH_3$, G=W=$R_2$'=$R_4$"=Hydrogen, and $R_3$" is —$CH_3$ To a solution of the compound from example 1 (83 mg, 0.1 mmol) in ethanol (10 ml) is added 10% Pd on carbon (20 mg). The mixture is stirred under hydrogen atmosphere at room temperature for 24 hours. The reaction mixture is then filtered and the filtrate is concentrated in vacuo, and the residue is purified via flash chromatography ($SiO_2$,2M $NH_3$ in methanol/$CH_2Cl_2$=5/95) to give the title compound (80 mg).

MS (ESI) m/z 789.99 (M+H)$^+$

Example 4

Compound of Formula V, wherein L is —CH$_2$CH$_3$, G=W=R$_4$"=Hydrogen, R$_2$'=R$_4$"=Ac, and R$_3$" is —CH$_3$ To a solution of the title compound of Example 1 (1.6 g, 2 mmol) in CH$_2$Cl$_2$ (15 ml) is added triethyl amine (1.17 ml, 8 mmol), acetic anhydride (0.57 ml, 6 mmol) and DMAP (244 mg, 2 mmol) at room temperature. The mixture is stirred at room temperature for 4 hours and quenched with saturated potassium carbonate (15 ml). The organic phase is separated and dried over Na$_2$SO$_4$. The solvent is then removed in vacuo, and the residue is purified via flash chromatography (SiO$_2$, hexane/acetone=1/1) to give the title compound (1.3 g).

MS (ESI) m/z 872.01 (M+H)$^{+13}$C NMR(CDCl$_3$): δ 176.8, 170.8, 170.3, 145.6, 114.3, 100.1, 95.9, 83.9, 83.3, 79.4, 79.1, 74.4, 74.3, 74.0, 73.2, 72.4, 69.5, 67.5, 64.5, 63.6, 63.3, 54.7, 49.6, 45.1, 41.9, 41.1, 40.4, 35.6, 31.4, 27.1, 26.9, 22.3, 21.9, 21.8, 21.5, 21.2, 21.1, 18.3, 16.7, 16.1, 11.1, 9.8, 7.6.

Example 5

Compound of Formula VI, wherein L is —CH$_2$CH$_3$ Y is Hydroxy, and G=W=R$_2$'=Hydrogen To a solution of the title compound of Example 1 (2.36 g, 3 mmol) in ethanol (15 ml) is added 2N HCl (15 ml) at room temperature. The resulting reaction mixture is heated to 70° C. and stirred at that temperature for 1 hour. The reaction is then quenched with saturated K$_2$CO$_3$ (20 ml) and extracted with ethyl acetate (50 ml). The extract is dried over Na$_2$SO$_4$ and the solvent is removed in vacuo. The residue is purified via flash chromatography (SiO$_2$,2M NH$_3$ in methanol/CH$_2$Cl$_2$=5/95) to give the title compound (1.8 g).

MS (ESI) m/z 629.91 (M+H)$^{+13}$C NMR(CDCl$_3$): δ 175.9, 145.6, 113.5, 106.9, 95.0, 84.9, 79.4, 76.7, 74.7, 74.3, 73.8, 70.7, 70.3, 65.9, 54.5, 53.7, 44.8, 42.0, 40.5, 36.4, 28.2, 27.0, 25.9, 21.5, 21.3, 21.2, 16.7, 16.4, 10.8, 8.2.

Example 6

Compound of Formula VI, wherein L is —CH$_2$CH$_3$, Y is Hydroxy, G=W=Hydrogen, and R$_2$'=TES To a solution of the title compound of Example 5 (4.4 g, 7 mmol) in DMF (25 ml) is added TES-Cl (3.5 ml, 21 mmol) and imidazole (0.95 g, 14 mmol) at room temperature. The mixture is stirred at room temperature for 2 hours, diluted with ethyl acetate (100 ml), washed with saturated K$_2$CO$_3$ (100 ml×1) and brine (100 ml×3), and dried over anhydrous Na$_2$SO$_4$. The solvent is removed in vacuo, and the residue is purified via flash chromatography (SiO$_2$, hexane/acetone=4/1) to give the title compound (4.5 g).

MS (ESI) m/z 744.16 (M+H)$^+$. $^{13}$C NMR(CDCl$_3$): δ 175.9, 145.6, 113.6, 102.2, 85.2, 84.7, 78.7, 76.9, 74.7, 74.3, 74.0, 73.1, 69.7, 68.9, 66.3, 64.8, 54.6, 44.1, 41.6, 41.2, 36.7, 36.3, 31.7, 29.1, 26.9, 26.2, 21.5, 21.4, 21.1, 16.8, 16.5, 10.8, 8.4, 7.7, 7.3, 6.8, 6.0, 5.5.

Example 7

Compound of Formula VI, wherein L is —CH$_2$CH$_3$, Y is Hydroxy, G=W=Hydrogen, and R$_2$'=Ac To a solution of the compound from Example 5 (5.03 g, 8 mmol) in CH$_2$Cl$_2$ (50 ml) was added acetic anhydride (1.5 ml, 16 mmol) at room temperature. The mixture was stirred at room temperature for over night and quenched with saturated NaHCO$_3$ (100 ml). Extracted with CH$_2$Cl$_2$ (50 ml) and dried over anhydrous Na$_2$SO$_4$. The solvent was removed in vacuo, and the residue was purified via flash chromatography (SiO$_2$, hexane/acetone=1/1) to give the title compound (5.1 g).

MS (ESI) m/z 671.64 (M+H)$^+$. $^{13}$C NMR(CDCl$_3$): δ 175.5, 170.2, 145.5, 113.8, 99.5, 85.2, 84.6, 78.4, 77.1, 76.9, 74.7, 74.2, 74.0, 71.6, 69.7, 68.8, 64.8, 63.1, 54.6, 44.0, 41.1, 40.3, 36.0, 31.2, 26.9, 26.0, 21.7, 21.6, 21.4, 21.3, 21.1, 16.7, 16.4, 10.8, 8.1, 7.5.

Example 8

Compound of Formula VI, L is —CH$_2$CH$_3$, G=W=Hydrogen, R$_2$' is Ac, and Y is (quinolin-3-yl)-allyloxy To a solution of the compound from Example 7 (126 mg, 0.2 mmol), quinolyl allyl Boc (114 mg, 0.4 mmol), and dppb (17 mg, 0.04 mmol) in THF (5 ml), is added Pd$_2$(dba)$_3$ (18.3 mg, 0.02 mmol) under nitrogen. The resulting reaction mixture is refluxed for 8 hours, diluted with ethyl acetate (25 ml), washed with saturated NaHCO$_3$ (20 ml×2) and brine (20 ml), and dried over anhydrous Na$_2$SO$_4$. The solvent is removed in vacuo, and the residue is purified by flash chromatography (SiO$_2$, hexane/acetone=1/1) to give the title compound (100 mg).

MS (ESI) m/z 838.76 (M+H)$^{+13}$C NMR(CDCl$_3$): δ175.7, 170.2, 149.3, 147.7, 145.6, 132.7, 130.0, 129.5, 129.1, 128.6, 128.3, 128.1, 128.0, 127.3, 113.7, 99.1, 85.6, 84.7, 83.4, 77.1, 74.7, 74.2, 74.1, 73.7, 72.0, 71.1, 69.5, 68.8, 64.7, 63.4, 54.6, 44.5, 40.8, 40.6, 37.3, 31.0, 26.9, 26.1, 21.8, 21.7, 21.3, 21.0, 16.7, 16.5, 10.9, 9.2, 7.3.

Example 9

Compound of Formula VI, L is —CH$_2$CH$_3$, G=W=R$_2$'=Hydrogen and Y is (quinolin-3-yl)-allyloxy A solution of the compound from Example 8 (100 mg, 0.12 mmol) in methanol (10 ml) is refluxed for 3 hours. The solvent is removed in vacuo, and the residue is purified via flash chromatography (SiO$_2$, 2M NH$_3$ in methanol/CH$_2$Cl$_2$=5/95) to give the title compound (80 mg).

MS (ESI) m/z 795.18 (M+H)$^{+13}$C NMR(CDCl$_3$): δ 175.8, 149.2, 147.7, 145.6, 132.9, 130.0, 129.5, 129.1, 128.3, 128.0, 127.3, 113.7, 101.4, 85.7, 84.7, 84.1, 74.7, 74.2, 74.0, 73.5, 71.1, 69.6, 69.2, 65.6, 64.7, 54.6, 44.5, 41.0, 40.3, 37.5, 29.0, 27.0, 26.2, 21.7, 21.5, 21.0, 16.7, 16.4, 10.9, 9.4, 7.4.

Example 10

Compound of Formula V, wherein L is —CH$_2$CH$_3$, W is —CH$_2$CH=CH$_2$, G is Hydrogen, R$_2$'=R$_4$"=Ac, and R$_3$" is —CH$_3$ To a solution of the compound from Example 4 (871 mg, 1 mmol), Allyl Boc (237 mg, 1.5 mmol) and dppb (43 mg, 0.1 mmol) in THF (10 ml) is added Pd$_2$(dba)$_3$ (46 mg, 0.05 mmol) under nitrogen. The mixture is refluxed for 3 hours, diluted with ethyl acetate (25 ml), washed with saturated NaHCO$_3$ (20 ml×2) and brine (20 ml), and dried over anhydrous Na$_2$SO$_4$. The solvent is removed in vacuo, and the residue is purified by flash chromatography ($SiO_2$, hexane/acetone=1/1) to give the title compound (0.9 g).

MS (ESI) m/z 911.99 $(M+H)^+$ $^{13}C$ NMR($CDCl_3$): δ 175.8, 170.8, 170.3, 146.4, 136.2, 115.6, 113.1, 99.7, 96.2, 83.3, 79.9, 78.9, 78.7, 75.2, 75.0, 74.2, 73.1, 72.4, 67.4, 66.5, 63.5, 63.4, 54.8, 49.5, 44.8, 41.5, 41.0, 35.7, 31.8, 31.3, 31.2, 27.2, 22.9, 22.2, 21.9, 21.8, 21.5, 21.3, 21.2, 19.1, 18.3, 16.4, 14.4, 10.8, 10.0.

Example 11

Compound of Formula VI, wherein L is —$CH_2CH_3$, W is —$CH_2CH=CH_2$, G=Hydrogen, Y is Hydroxy, and $R_2'$ is Ac To a solution of the compound from Example 10 (0.27 g, 0.3 mmol) in isopropanol (5 ml) is added 2N HCl (5 ml). The mixture is stirred at 60° C. for 30 minutes, quenched with saturated $K_2CO_3$ (20 ml), extracted with ethyl acetate (30 ml), washed with brine (30 ml×2), and dried over anhydrous $Na_2SO_4$. The solvent is removed in vacuo, and the residue is purified by flash chromatography ($SiO_2$, hexane/acetone=1/1) to give the title compound (0.2 g).

MS (ESI) m/z 711.89 $(M+H)^+$

Example 12

Compound of Formula VI, wherein L is —$CH_2CH_3$, W is —$CH_2CH=CH_2$, Y is Hydroxy, and G=R='=Hydrogen A solution of the compound from Example 11 (100 mg, 0.14 mmol) in methanol (10 ml) is stirred at 60° C. for overnight. The solvent is removed in vacuo and the residue is purified via flash chromatography ($SiO_2$, 2M $NH_3$ in methanol/$CH_2Cl_2$=5/95) to give the title compound (90 mg).

MS (ESI) m/z 669.69 $(M+H)^+$

Example 13

Compound of Formula I, wherein A and B are Taken Together with the Carbon Atom to which They are Attached to Form C=$CH_2$, L is —$CH_2CH_3$, W=G=Z=$R_2'$=Hydrogen, and X and Y Taken Together are oxo Step 13a. Compound of formula Ie, wherein L is —$CH_2CH_3$, G is hydrogen, W=—$CH_2CH=CH_2$, and $R_2'$ is Ac.

To a solution of the title compound of Example 11 (100 mg, 0.14 mmol) in $CH_2Cl_2$ (5 ml) is added Dess-Martin reagent (85 mg, 0.2 mmol) and acetic acid (0.1 ml) at room temperature. The resulting reaction mixture is stirred at room temperature for 3 hours and quenched with 5% $NaS_2O_3$ (5 ml). The organic phase is separated and dried over anhydrous $Na_2SO_4$. The solvent is removed in vacuo, and the residue is purified by flash chromatography ($SiO_2$, hexane/acetone=1/1) to give the title compound (90 mg).

MS (ESI) m/z 709.76 $(M+H)^+$

Step 13b.

A solution of the compound from step 13a (100 mg, 0.14 mmol) in methanol (10 ml) is stirred at 60° C. overnight. The solvent is removed in vacuo and the residue is purified via flash chromatography ($SiO_2$, 2M $NH_3$ in methanol/$CH_2Cl_2$=5/95) to give the title compound (90 mg).

MS (ESI) m/z 667.69 $(M+H)^+$ $^{13}C$ NMR($CDCl_3$): δ 176.3, 136.6, 115.7, 106.1, 103.1, 95.2, 83.9, 82.5, 79.6, 77.2, 74.9, 70.1, 69.8, 65.7, 58.9, 53.7, 50.0, 49.1, 41.2, 40.6, 28.9, 27.0, 26.8, 22.4, 21.5, 21.4, 16.8, 14.4, 14.3, 13.6, 11.1.

Example 14

Compound of Formula I, wherein A and B are Taken Together with the Carbon Atom to which They are Attached to Form C=$CH_2$, L is —$CH_2CH_3$, G=W=X=Z=Hydrogen, $R_2'$=Ac and Y is —OC(O)(p-nitrophenyl)

The title compound is prepared from the title compound of Example 7, sodium hydride, and p-nitrobenzoyl fluoride according to the procedures set forth in U.S. Pat. No. 5,602,239 (1997).

Example 15

Compound of Formula I, wherein A and B are Taken Together with the Carbon Atom to which They are Attached to Form C=$CH_2$, L is —$CH_2CH_3$, G=W=X=Z=$R_2'$=Hydrogen, and Y is —OC(O)(p-nitrophenyl)

The title compound is prepared with the title compound of Example 14 by the procedure described in Step 13b of Example 13.

Example 16

Compound of Formula I, wherein A and B are Taken Together with the Carbon Atom to which They are Attached to Form C=$CH_2$, L is —$CH_2CH_3$, G=W=X=Z=Hydrogen, $R_2'$=Ac, and Y is —OC(O)(2-nitro-4-trifluoromethylphenyl)

The title compound is prepared via the method delineated in Example 14 from the title compound of Example 7, sodium hydride, and 2-nitro-4-trifluoromethylbenzoyl fluoride.

Example 17

Compound of Formula I, wherein A and B are Taken Together with the Carbon Atom to which They are Attached to Form C=$CH_2$, L is —$CH_2CH_3$, G=W=X=Z=$R_2'$=Hydrogen and Y is —OC(O)(2-nitro-4-trifluoromethylphenyl)

The title compound is prepared with the title compound of Example 16 by the procedure described in Step 13b of Example 13.

Example 18

Compound of Formula I, wherein A and B are Taken Together with the Carbon Atom to which They are Attached to Form C=$CH_2$, L is —$CH_2CH_3$, G=W=X=Z=Hydrogen, $R_2'$=Ac, and Y is —OC(O)$CH_2$(p-methoxyphenyl)

The title compound is prepared from the title compound of Example 7, p-methoxyphenylacetic acid, pivaloyl chloride, and triethylamine in a solution of pyridine and dichloromethane according to the procedure delineated in EP 0 679 320 B1 or WO 99/21868.

Example 19

Compound of Formula I, wherein A and B are Taken Together with the Carbon Atom to which They are Attached to Form C=CH$_2$, L is —CH$_2$CH$_3$, G=W=X=Z=R$_2$'=Hydrogen, and Y is —OC(O)CH$_2$(p-methoxyphenyl)

The title compound is prepared with the title compound of Example 18 by the procedure described in Step 13b of Example 13.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by formula (I):

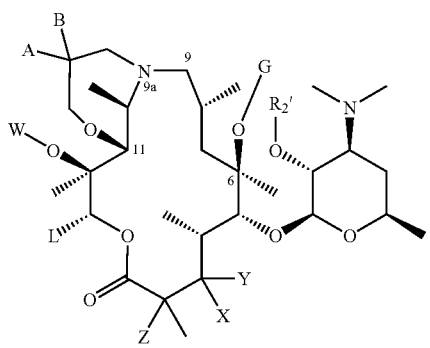

or a pharmaceutically acceptable salt, or ester thereof, wherein:

A is
- (a) —OR$_p$, where R$_p$ is a hydroxy protecting group;
- (b) —R$_1$, where R$_1$ is independently aryl, substituted aryl, heteroaryl, or substituted heteroaryl;
- (c) —OR$_1$, where R$_1$ is as previously defined;
- (d) —R$_2$, where R$_2$ independently is
  - (1) hydrogen;
  - (2) —C$_1$-C$_6$ alkyl containing 0, 1, 2, or 3 heteroatoms selected from O, S or N, optionally substituted with one or more substituents selected from halogen, aryl, substituted aryl, heteroaryl, or substituted heteroaryl;
  - (3) —C$_2$-C$_6$ alkenyl containing 0, 1, 2, or 3 heteroatoms selected from O, S, or N, optionally substituted with one or more substituents selected from halogen, aryl, substituted aryl, heteroaryl, or substituted heteroaryl; or
  - (4) —C$_2$-C$_6$ alkynyl containing 0, 1, 2, or 3 heteroatoms selected from O, S or N, optionally substituted with one or more substituents selected from halogen, aryl, substituted aryl, heteroaryl, or substituted heteroaryl;
- (e) —OR$_2$, where R$_2$ is previously defined;
- (f) —S(O)$_n$R$_{11}$, where n=0, 1 or 2, and R$_{11}$ is independently R$_1$ or R$_2$, where R$_1$ and R$_2$ are as previously defined;
- (g) —NHC(O)R$_{11}$, where R$_{11}$ is as previously defined;
- (h) —NHC(O)NHR$_{11}$, where R$_{11}$, is as previously defined;
- (i) —NHS(O)$_2$R$_{11}$, where R$_{11}$ is as previously defined;
- (j) —NR$_{14}$R$_{15}$, where R$_{14}$ and R$_{15}$ are each independently R$_{11}$, where R$_{11}$ is as previously defined; or
- (k) —NHR$_3$, where R$_3$ is an amino protecting group;

B is
- (a) deuterium;
- (b) halogen;
- (c) —OH;
- (d) —R$_1$, where R$_1$ is as previously defined;
- (e) —R$_2$, where R$_2$ is as previously defined; or
- (f) —OR$_p$, where R$_p$ is as previously defined, provided that when B is halogen, —OH or OR$_p$, A is R$_1$ or R$_2$, where R$_1$ and R$_2$ are previously defined;

or, alternatively, A and B taken together with the carbon atom to which they are attached are
- (a) C=O;
- (b) C(OR$_2$)$_2$, where R$_2$ is as previously defined;
- (c) C(SR$_2$)$_2$, where R$_2$ is as previously defined;
- (d) C(OR$_{12}$)(OR$_{13}$), where R$_{12}$ and R$_{13}$ taken together are —(CH$_2$)$_m$—, and where m is 2 or 3;
- (e) C(SR$_{12}$)(SR$_{13}$), where R$_{12}$ and R$_{13}$ taken together are —(CH$_2$)$_m$—, where m is as previously defined;
- (f) C=CHR$_{11}$, where R$_{11}$ is as previously defined;
- (g) C=N—O—R$_{11}$, where R$_{11}$ is as previously defined;
- (h) C=NNHR$_{11}$, where R$_{11}$ is as previously defined;
- (i) C=NNHC(O)R$_{11}$, where R$_{11}$ is as previously defined;
- (j) C=NNHC(O)NHR$_{11}$, where R$_{11}$ is as previously defined;
- (k) C=NNHS(O)$_2$R$_{11}$, where R$_{11}$ is as previously defined;
- (l) C=NNHR$_3$, where R$_3$ is as previously defined; or
- (m) C=NR$_{11}$, where R$_{11}$ is as previously defined;

G is
- (a) hydrogen;
- (b) —C$_1$-C$_6$ alkyl, containing 0, 1, 2, or 3 heteroatoms selected from O, S or N, optionally substituted with one or more substituents selected from halogen, aryl, substituted aryl, heteroaryl, or substituted heteroaryl;
- (c) —C$_2$-C$_6$ alkenyl, containing 0, 1, 2, or 3 heteroatoms selected from O, S or N, optionally substituted with one or more substituents selected from halogen, aryl, substituted aryl, heteroaryl, or substituted heteroaryl;
- (d) —C$_2$-C$_6$ alkynyl, containing 0, 1, 2, or 3 heteroatoms selected from O, S or N, optionally substituted with one or more substituents selected from halogen, aryl, substituted aryl, heteroaryl, or substituted heteroaryl;

provided that when A and G and are hydrogen, B is not hydrogen or deuterium;

L is
- (a) —CH(OH)CH$_3$;
- (b) —C$_1$-C$_6$ alkyl, optionally substituted with one or more substituents selected from aryl, substituted aryl, heteroaryl, or substituted heteroaryl;
- (c) —C$_2$-C$_6$ alkenyl, optionally substituted with one or more substituents selected from aryl, substituted aryl, heteroaryl, or substituted heteroaryl; or
- (d) —C$_2$-C$_6$ alkynyl, optionally substituted with one or more substituents selected from aryl, substituted aryl, heteroaryl, or substituted heteroaryl;

W is selected from:
(a) hydrogen;
(b) $R_8$, where $R_8$ is $C_1$-$C_6$-alkyl, $C_2$-$C_6$-alkenyl or $C_2$-$C_6$-alkynyl, optionally substituted with one or more substituents selected from:
  (1) halogen;
  (2) aryl;
  (3) substituted-aryl;
  (4) heteroaryl;
  (5) substituted-heteroaryl;
  (6) —O—$C_1$-$C_6$-alkyl-$R_{11}$, where $R_{11}$ is as previously defined; and
  (7) —N($R_{14}R_{15}$), where $R_{14}$ and $R_{15}$ are as previously defined;
(c) —C(O)$R_{11}$, where $R_{11}$, where $R_{11}$ is as previously defined;
(d) —C(O)O—$R_{11}$, where $R_{11}$ is as previously defined; and
(e) —C(O)N($R_{14}R_{15}$), where $R_{14}$ and $R_{15}$ are as previously defined;
X is hydrogen;
Y is
(a) hydrogen;
(b) —OH;
(c) —O$R_p$, where $R_p$ is as previously defined;
(d) —O$R_{11}$, where $R_p$ is as previously defined;
(e) —OC(O)$R_{11}$, where $R_{11}$ is as previously defined;
(f) —OC(O)NH$R_{11}$, where $R_{11}$ is as previously defined;
(g) —S(O)$_n R_{11}$, where n and $R_{11}$ are as previously defined;

(h)

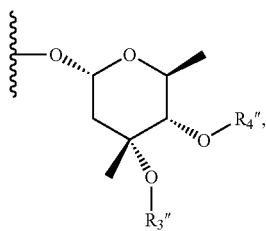

where $R_3''$ is selected from hydrogen or methyl and $R_4''$ is selected from:
(1) hydrogen;
(2) $R_p$, where $R_p$ is as previously defined; or
(3) —C(O)(CH$_2$)$_k$-M-$R_{11}$, wherein $R_{11}$ is as previously defined, k is 2 to 8, and M is absent or -Q(CH$_2$)$_q$Q'-, where q=an integer from 2 to 8, and Q and Q' are independently selected from:
  i) —N($R_{20}$)—, where $R_{20}$ is $R_{11}$ is as previously defined;
  ii) —O—;
  iii) —S(O)$_n$—, where n is as previously defined;
  iv) —N($R_{20}$)C(O)—, where $R_{20}$ is as previously defined;
  v) —C(O)N($R_{20}$)—, where $R_{20}$ is as previously defined; or
  vi) —N[C(O)$R_{20}$]—, where $R_{20}$ is as previously defined; and
in the alternative, X and Y combined together are oxo;

Z is
(a) hydrogen;
(b) methyl; or
(c) halogen; and
$R_2'$ is hydrogen or $R_p$, where $R_p$, is as previously defined.

2. A compound according to claim 1 of formula II:

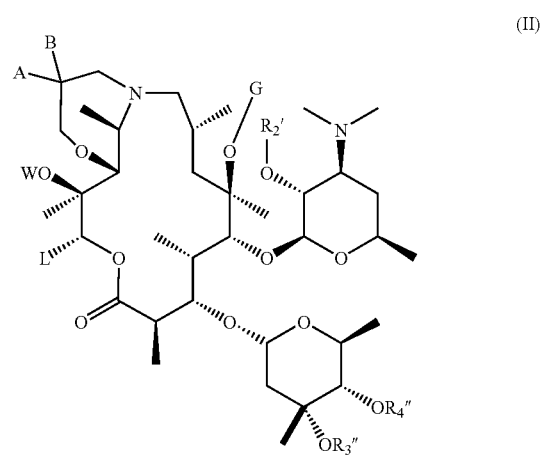

(II)

wherein A, B, G, L, W, $R_2'$, $R_3''$, and $R_4''$ are as defined in claim 1.

3. A compound according to claim 1 of formula III:

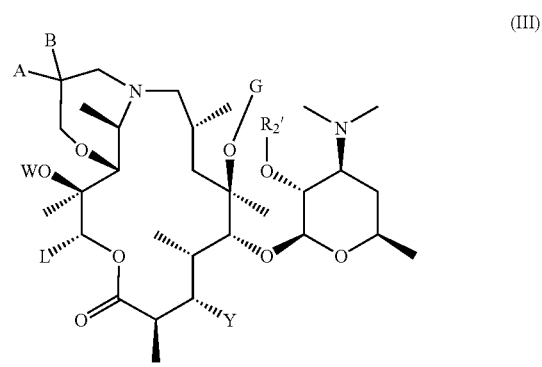

(III)

wherein A, B, G, L, W, Y, and $R_2'$ are as defined in claim 1.

4. A compound according to claim 1 of formula IV:

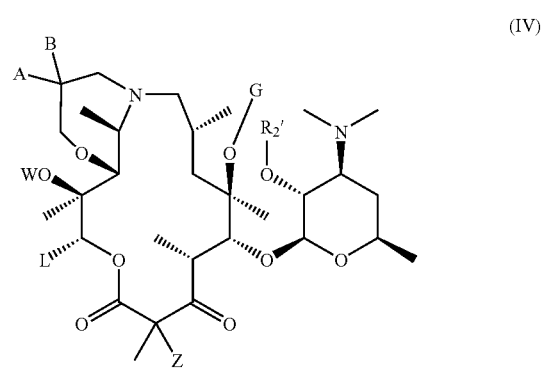

(IV)

wherein G, L, W, Z, and $R_2'$ are as defined in claim 1.

5. A compound according to claim 1 of formula V:

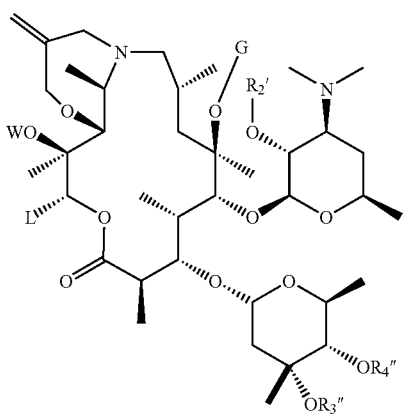

(V)

wherein G, L, W, $R_2'$, $R_3''$, and $R_4''$ are as defined in claim 1.

6. A compound according to claim 1 of formula VI:

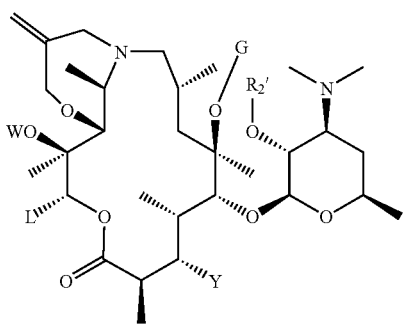

(VI)

wherein G, L, W, Y, and $R_2'$ are as defined in claim 1.

7. A compound according to claim 1 of formula VII:

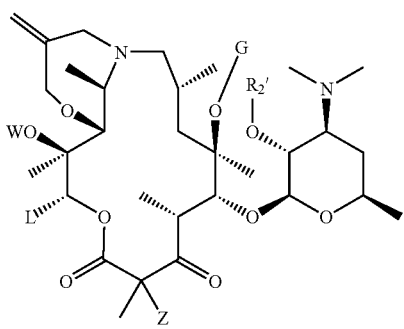

(VII)

wherein G, L, W, Z, and $R_2'$ are as defined in claim 1.

8. A method for treating a bacterial infection in a subject in need of such treatment, comprising administering to said subject a compound according to claim 1.

9. A pharmaceutical composition comprising a compound of claim 1 or a pharmaceutically acceptable salt, or ester thereof, in combination with a pharmaceutically acceptable carrier.

10. A method for controlling a bacterial infection in a subject, comprising administering to said subject a pharmaceutical composition according to claim 9.

11. A process for producing compounds of formula I, according to claim 1, wherein A and B taken together with the carbon atom to which they are attached are C=CH—$R_{11}$, comprising the step of reacting a compound of the formula Ia:

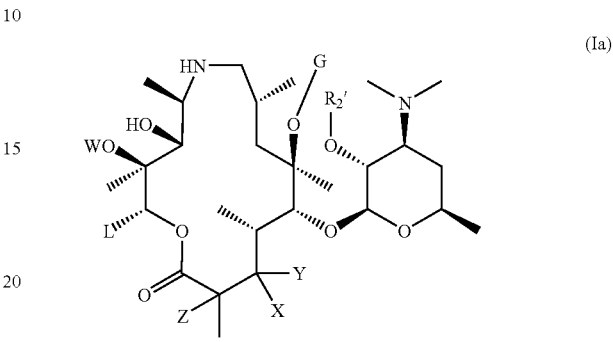

(Ia)

wherein:
(1) X is hydrogen,
(2) Y is

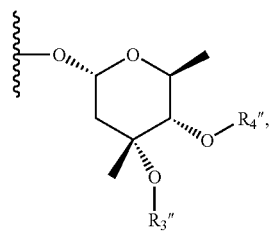

where $R_3''$ and $R_4''$ are as defined in claim 1; and
(3) G, L, W, Z, and $R_2'$ are as defined in claim 1, with

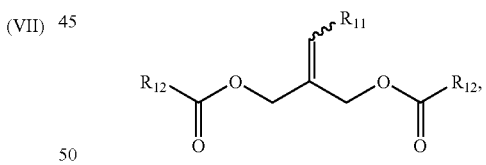

wherein $R_{11}$ is as defined in claim 1 and $R_{12}$ is —$R_{11}$ or —$OR_{11}$ where $R_{11}$ is as defined in claim 1.

12. The method of claim 11, wherein the step of reacting occurs in the presence of a phosphine ligand and Pd(0) catalyst.

13. The method of claim 12, wherein the step of reacting occurs under reflux conditions.

14. The method of claim 13, wherein the step of reacting occurs optionally in the presence of an organic acid.

15. A compound of claim 1 selected from:
(a) Compound of formula I, wherein A and B are taken together with the carbon atom to which they are attached to form C=CH$_2$, L is —CH$_2$CH$_3$, W=G=Z=$R_2'$=hydrogen, and X and Y taken together are oxo;

(b) Compound of formula I, wherein A and B are taken together with the carbon atom to which they are attached to form C=$CH_2$, L is —$CH_2CH_3$, W=X=G=Z=hydrogen, $R_2$'=Ac, and Y is —OC(O)(p-nitrophenyl);

(c) Compound of formula I, wherein A and B are taken together with the carbon atom to which they are attached to form C=$CH_2$, L is —$CH_2CH_3$, W=X=G=Z=$R_2$'=hydrogen, and Y is —OC(O)(p-nitrophenyl);

(d) Compound of formula I, wherein A and B are taken together with the carbon atom to which they are attached to form C=$CH_2$, L is —$CH_2CH_3$, W=X=G=Z=hydrogen, $R_2$'=Ac, and Y is —OC(O)(2-nitro-4-trifluoromethylphenyl);

(e) Compound of formula I, wherein A and B are taken together with the carbon atom to which they are attached to form C=$CH_2$, L is —$CH_2CH_3$, W=X=G=Z=$R_2$'=hydrogen, and Y is —OC(O)(2-nitro-4-trifluoromethylphenyl);

(f) Compound of formula I, wherein A and B are taken together with the carbon atom to which they are attached to form C=$CH_2$, L is —$CH_2CH_3$, W=X=G=Z=hydrogen, $R_2$'=Ac, and Y is —OC(O)$CH_2$(p-methoxyphenyl); or (g) Compound of formula I, wherein A and B are taken together with the carbon atom to which they are attached to form C=$CH_2$, L is —$CH_2CH_3$, W=X=G=Z=$R_2$'=hydrogen, and Y is —OC(O)$CH_2$(p-methoxyphenyl).

16. A compound of claim 2 selected from:

(a) Compound of formula II, wherein A and B taken together with the carbon atom to which they are attached are C=$CH_2$, L is —$CH_2CH_3$, G=W=$R_2$'=$R_4$"=hydrogen, and $R_3$" is methyl;

(b) Compound of formula II, wherein A and B taken together with the carbon atom to which they are attached are C=$CH_2$, L is —$CH_2CH_3$, G=W=$R_4$"=hydrogen, $R_2$' is Ac, and $R_3$" is —$CH_3$; or (c) Compound of formula II, wherein A is hydrogen, B is —$CH_3$, L is —$CH_2CH_3$, G=W=$R_2$'=$R_4$"=hydrogen, and $R_3$" is —$CH_3$.

17. A compound of claim 5 selected from:

(a) Compound of formula V, wherein L is —$CH_2CH_3$, G=W=$R_4$"=hydrogen, $R_2$'=$R_4$"=Ac, and $R_3$" is —$CH_3$; or (b) Compound of formula V, wherein L is —$CH_2CH_3$, W is —$CH_2CH$=$CH_2$, G is hydrogen, $R_2$'=$R_4$"=Ac, and $R_3$" is —$CH_3$.

18. A compound of claim 6 selected from:

(a) Compound of formula VI, wherein L is —$CH_2CH_3$ Y is hydroxy, and G=W=$R_2$'=hydrogen;

(b) Compound of formula VI, wherein L is —$CH_2CH_3$, Y is hydroxy, G=W=hydrogen, and $R_2$'=TES;

(c) Compound of formula VI, wherein L is —$CH_2CH_3$, Y is hydroxy, G=W=hydrogen, and $R_2$'=Ac;

(d) Compound of formula VI, L is —$CH_2CH_3$, G=W=hydrogen, $R_2$' is Ac, and Y is (quinolin-3-yl)-allyloxy;

(e) Compound of formula VI, L is —$CH_2CH_3$, G=W=$R_2$'=hydrogen, and Y is (quinolin-3-yl)-allyloxy;

(f) Compound of formula VI, wherein L is —$CH_2CH_3$, W is —$CH_2CH$=$CH_2$, =hydrogen, Y is hydroxy, and $R_2$' is Ac; or (g) Compound of formula VI, wherein L is —$CH_2CH_3$, W is —$CH_2CH$=$CH_2$, Y is hydroxy, and G=$R_2$'=hydrogen.

* * * * *

UNITED STATES PATENT AND TRADEMARK OFFICE
CERTIFICATE OF CORRECTION

| | | |
|---|---|---|
| PATENT NO. | : 7,276,487 B2 | Page 1 of 1 |
| APPLICATION NO. | : 10/946339 | |
| DATED | : October 2, 2007 | |
| INVENTOR(S) | : Wang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 243 days.

Signed and Sealed this

Fourth Day of January, 2011

David J. Kappos
*Director of the United States Patent and Trademark Office*